(12) United States Patent
Bierganns et al.

(10) Patent No.: US 8,343,469 B2
(45) Date of Patent: Jan. 1, 2013

(54) CATIONIC SYNTHETIC POLYMERS WITH IMPROVED SOLUBILITY AND PERFORMANCE IN SURFACTANT-BASED SYSTEMS AND USE IN PERSONAL CARE AND HOUSEHOLD APPLICATIONS

(75) Inventors: Patric Bierganns, Krefeld (DE); Paquita Erazo-Majewicz, Landenberg, PA (US); Nabil Naouli, Wilmington, DE (US)

(73) Assignee: Hercules Incorporated, Wilmington, DE (US)

(*) Notice: Subject to any disclaimer, the term of this patent is extended or adjusted under 35 U.S.C. 154(b) by 0 days.

(21) Appl. No.: 12/828,853

(22) Filed: Jul. 1, 2010

(65) Prior Publication Data

US 2011/0002868 A1 Jan. 6, 2011

Related U.S. Application Data

(60) Provisional application No. 61/222,685, filed on Jul. 2, 2009.

(51) Int. Cl.
| | |
|---|---|
| A61K 8/81 | (2006.01) |
| A61K 8/73 | (2006.01) |
| A61K 31/355 | (2006.01) |
| A61K 8/18 | (2006.01) |
| A61Q 5/06 | (2006.01) |
| A61Q 5/02 | (2006.01) |

(52) U.S. Cl. ............... 424/70.16; 424/70.17; 424/70.13; 514/188; 510/119

(58) Field of Classification Search ............... 424/70.13, 424/70.16, 70.17; 510/119; 514/188
See application file for complete search history.

(56) References Cited

U.S. PATENT DOCUMENTS

| | | | |
|---|---|---|---|
| 5,221,530 | A | 6/1993 | Janchitraponvej et al. |
| 5,417,965 | A | 5/1995 | Janchitraponvej et al. |
| 5,756,436 | A | 5/1998 | Royce et al. |
| 6,495,498 | B2 | 12/2002 | Niemiec et al. |
| 6,849,584 | B2 | 2/2005 | Geary et al. |
| 7,067,499 | B2 | 6/2006 | Erazo-Majewicz et al. |
| 7,375,173 | B2 | 5/2008 | Steiner et al. |
| 7,781,386 | B2 | 8/2010 | Ainger et al. |
| 2002/0077256 | A1 | 6/2002 | Niemiec et al. |
| 2008/0112906 | A1 | 5/2008 | Erazo-Majewicz et al. |
| 2008/0112907 | A1 | 5/2008 | Chan et al. |
| 2008/0317698 | A1* | 12/2008 | Wells et al. ................. 424/78.08 |
| 2010/0179082 | A1* | 7/2010 | Castro et al. .................. 510/119 |

FOREIGN PATENT DOCUMENTS

| | | |
|---|---|---|
| DE | 3544909 A1 | 6/1987 |
| WO | 2004/091557 A2 | 10/2004 |
| WO | 2007/065537 A1 | 6/2007 |
| WO | 2008/129493 A2 | 10/2008 |

OTHER PUBLICATIONS

International Search Report and Written Opinion mailed Nov. 4, 2010.

* cited by examiner

*Primary Examiner* — Blessing Fubara

(74) *Attorney, Agent, or Firm* — Wood, Herron & Evans, L.L.P.

(57) ABSTRACT

The present invention is related to surfactant-based formulations comprising the polyelectrolytes and blends of such polyelectrolytes with non-cellulosic cationic polysaccharide polymers. The surfactant-based formulations exhibit improved clarity of the resulting formulations, their improved conditioning of keratin substrates, textile substrates, and hard-surface substrates, their improved deposition of dispersed phase materials onto keratin substrates, textile substrates, and hard-surface substrates, their improved lather performance, and their improved rheology in applications such as personal care and household care products and textile applications.

18 Claims, 2 Drawing Sheets

CATIONIC SYNTHETIC POLYMERS WITH IMPROVED SOLUBILITY AND PERFORMANCE IN SURFACTANT-BASED SYSTEMS AND USE IN PERSONAL CARE AND HOUSEHOLD APPLICATIONS

RELATED APPLICATION

This application is related to and claims the benefit of U.S. Provisional Patent Application Ser. No. 61/222,685, filed on Jul. 2, 2009.

FIELD OF THE INVENTION

The present invention relates to surfactant-based formulations, particularly surfactant based formulations comprising polymer compositions, especially a surfactant-based cleansing composition comprising, a surfactant, cationic, water-soluble polyelectrolytes and use of the same in personal care and household care cleansing compositions for treating keratinous substrates, textile substrates, and hard-surface substrates.

Surfactant-based formulations comprising the polyelectrolytes of the invention and blends of such polyelectrolytes with non-cellulosic cationic polysaccharide polymers such as cationic polygalactomannan polymers and derivatized cationic polygalactomannan polymers are desirable for the improved clarity of the resulting formulations, their improved conditioning of keratin substrates, textile substrates, and hard-surface substrates, their improved deposition of dispersed phase materials onto keratin substrates, textile substrates, and hard-surface substrates, their improved lather performance, and their improved rheology in applications such as personal care and household care products and textile applications.

BACKGROUND OF THE INVENTION

Surfactant-based personal care compositions containing cationic water-soluble polyelectrolytes have been found to deliver good conditioning performance to hair and skin substrates. The cationic water-soluble polyelectrolyte polymers can be based on polysaccharide backbones or on synthetic polymer backbones such as acrylamide, methacrylamide, acrylate esters, methacrylate esters, or vinyl pyrrolidone, for example.

Non-cellulosic cationic polysaccharides such as cationic guars, marketed under the trade names N-Hance® or Jaguar® cationic guars, are commonly used as conditioners in products such as shampoos, 2-in-1 or 3-in-1 conditioning shampoos and body washes, laundry detergents, and shampoos to provide conditioning to the hair, conditioning effects to the skin, or to provide conditioning, softening, and antistatic characteristics to fabrics.

Personal care compositions containing cationic oxidized polysaccharides, including cationic oxidized guar compositions, have been found to deliver good conditioning performance to hair and skin substrates, as described in WO2004/091557 and U.S. Pat. No. 7,067,499. The molecular weight of the cationic guar can vary from as low a molecular weight as 10,000 to as high as several million, and have good performance as a conditioning agent. The use of cationic, anionic, amphoteric or hydrophobic acrylamide polymers in conjunction with cationic oxidized polysaccharides such as cationic oxidized guars has been described in WO2004/091557 and U.S. Pat. No. 7,067,499 and in other documents such as WO2006/026750 in combination with cationic guar.

Cationic polyelectrolyte polymers based on synthetic polymers backbones have also found use as conditioning agents and deposition agents in personal care formulations. In U.S. Pat. No. 5,221,530, crosslinked quaternary acrylate/acrylamide copolymers have been disclosed as delivering good wet and dry conditioning and high levels of foam to shampoo and cleansing formulations when used alone and in U.S. Pat. No. 5,417,965, a combination with polyethyleneimine is taught.

In U.S. Pat. No. 5,756,436, non-crosslinked cationic water-soluble polyelectrolytes based on synthetic polymer backbones having charge densities>4 meq/g have been described for use as deposition polymers in conditioning shampoos containing water-insoluble conditioning agents.

In U.S. Pat. No. 6,849,584, non-crosslinked cationic water-soluble polyelectrolytes based on synthetic polymer backbones having a charge density>2 meq/gram have also been described in personal cleansing compositions containing water-insoluble solid particulate materials and phase separation initiators.

In U.S. Pat. No. 6,495,498, a cleansing composition containing combinations of cationic polyelectrolyte polymers has also been described, where one polymer is a cationic polygalactomannan such as cationic guar and another polymer may be a cationic water-soluble synthetic copolymer in the presence of a water-soluble silicone conditioning agent.

In WO2007/065537, an aqueous shampoo composition containing combinations of cationic polymers has also been described, containing dispersed phase droplets of a water insoluble conditioning agent<4 micron in droplet diameter, where one polymer is a cationic polygalactomannan such as cationic guar and another polymer may be a cationic acrylamide copolymer having a charge density<1 meq/gram.

In WO2008/129493, personal cleansing compositions containing combinations of cationic polymers have also been described, where one polymer is a cationic polymer having a charge density<4 meq/g and which forms an isotropic coacervate with the anionic surfactant and the second cationic polymer having a charge density>4 meq/g that forms a lyotropic liquid crystal on combination with the anionic surfactant.

Although these documents demonstrate that cationic polyelectrolyte polymers based on synthetic polymer backbones can deliver conditioning and enhance deposition of silicone and zinc from surfactant-based formulations, the commercial cationic synthetic polyelectrolyte polymers currently available in the marketplace are high in molecular weight, and as a result, impart a "stringy" rheology to surfactant-based formulations. The lower MW cationic synthetic polyelectrolyte polymers that are currently available in the marketplace, have some drawbacks as well such as reduced solubility, reduced clarity and reduced deposition performance in surfactant-based formulas. The cationic, anionic, and nonionic synthetic polyelectrolytes available in the marketplace also contain high levels of residual monomers, such as acrylamide monomer. There is a need to reduce the residual monomer level in these compositions to lower levels.

In addition, the hydrolytic stability of cationic synthetic polyelectrolytes such as cationic(meth)acrylic acid ester polymers is an important aspect of their performance in aqueous formulations. In DE 3544909, cationic synthetic polyelectrolyte polymers derived from poly(meth)acrylic acid esters are susceptible to hydrolysis of the ester functionality in aqueous solutions, with lifetimes ranging from hours to days, at pH values of 6-7.5. In addition, these cationic synthetic polyelectrolyte polymers have high acute aquatic toxicity, depending on their charge density. When the ester function is hydrolyzed, these polymers have much lower ecotoxicity, see Chang et al, "Water Science Technology", Vol. 44, No. 2-3, 461-468, 2001.

In U.S. Pat. No. 7,375,173, the disclosure of which is hereby incorporated by reference in its entirety, it has been found that cationic synthetic polyelectrolyte terpolymers of improved ecotoxicity can be prepared from polymerization of monomers of (meth)acrylamide, a quaternized (meth)acrylamide derivative, and a (meth)acrylic acid derivative and or hydrolysis stable cationic monomers. This finding is introduced here as reference and is incorporated as part of the disclosure.

Wet and dry measurements are typical test methods used to measure conditioning performance in shampoo and conditioner applications. Commercial conditioning polymers currently available in the marketplace have been reported to reduce the wet combing force experienced on combing wet hair by 30%-80% relative to a shampoo containing no polymer.

Conditioning performance in a shampoo application can also be measured by monitoring the decrease in optical transmittance of a transparent shampoo or cleansing formulation containing conditioning polymers on increasing dilution with water. The larger the drop in transmittance on dilution with water, the greater the level of deposition. The drop in transmittance or decrease in optical clarity of the formulation is associated with precipitation of the conditioning polymer from the shampoo or other cleansing formulation. The conditioning polymer can be deposited in the form of a complex with surfactants in the formulation or in an uncomplexed form.

The amount of silicone, other conditioning oils or functional materials, zinc, or other active or performance material deposited onto hair or the scalp from a shampoo, conditioner, or colorant system, onto skin from a cleansing or conditioning body wash, or onto fabric from a surfactant-based laundry formulation is also a measure of the conditioning or deposition performance of a conditioning or deposition polymer. The uniformity or nonuniformity of deposition of the silicone, other conditioning oils or conditioning materials, zinc, fragrance, or other "active" material can have significant impact on the perceived performance of the cosmetic formulation. The deposition profile is especially important on substrates such as: 1) hair fibers, where deposition along the fiber, from root to tip, is needed to ameliorate the damage in areas toward the tip or end of the hair fiber and to deposit color uniformly from hair coloring formulations and maintain color uniformity along the fibers; 2) on skin, especially in dry or damaged areas of the skin, where deposition of oils, other conditioning agents, active materials such as antimicrobial agents, sunscreen actives, or colorants such as self-tanning ingredients is needed to occur uniformly; and 3) on fabrics, where deposition occurs, especially on damaged or worn areas, of fabrics such as wool, cotton, polyester.

In skincare applications, skin lubricity or reduced friction or softer feel of the skin, reduced water vapor transmission and improved skin elasticity are test methods used to measure skin conditioning. In surfactant-based household cleansing product formulations where conditioning performance is desired, such as dish detergents, laundry detergents, fabric softeners, and antistatic products, conditioning refers to imparting a softer feel to the hands with liquid dish washing soaps or to fabric with laundry detergents or fabric softeners, and eliminating static effects, eliminating fabric fiber breakage or deformation known as pilling. Imparting color retention or color vibrancy properties to fabrics is also important and can be measured.

Although commercial cationic water-soluble synthetic polyelectrolyte polymers have been shown to deliver conditioning and enhance deposition of silicone and zinc from surfactant-based formulations, the commercial water-soluble synthetic polyelectrolyte polymers available in the marketplace are high in molecular weight, and as a result, they impart a stringy rheology to the surfactant-based formulations. Lower MW cationic water-soluble synthetic polyelectrolyte polymers in the marketplace, have some drawbacks such as reduced clarity in surfactant-based formulations, reduced solubility in surfactant-based formulations, and reduced deposition performance in surfactant-based formulations.

Although non-cellulosic cationically modified polysaccharides and cationic water-soluble polyelectrolyte polymers based on synthetic backbones are known to perform as conditioning polymers in surfactant based cleansing formulations and as deposition aids for conditioning oils and active treatment delivery to the hair and skin, the repeated use of these polymers can confer unwanted buildup of conditioning components, such as silicone and other oils, on the hair or skin. This buildup is apparent as an increase in the energy needed to comb through the dry hair, and as a sticky feel to the hair. In addition, these polymers deliver more conditioning to the root end of the hair fiber, and there is a need to create polymer compositions that deliver more uniform deposition of silicone and other actives along the length of the hair fiber, to the middle section and tip of the hair fiber, where the fiber is more damaged and in need of more conditioning. Finally, in the area of antidandruff and delivery of antimicrobial active materials to the scalp, there is a need for increasing the efficiency of delivery of antimicrobial compound from surfactant systems such as shampoos and hand cleansers, as well as better targeting delivery to the scalp and skin, and maintaining it in place for prolonged activity.

There exists a need for improved deposition and deposition profiles of materials such as silicone, fragrance, zinc, and other active materials onto the hair and scalp, from surfactant-based formulations, without undesirable stringiness imparted to the formulation by the surfactants or polymers used in these formulations. There also exists a need for surfactant-based formulations which improve the amount of deposit for oil phases such as silicone, fragrance oils, mineral oil, and particulate materials, such as zinc pyrithione, zinc carbonate, and other active materials, where the lather or foaming property of the composition is maintained or improved.

There is also a need for polymer compositions containing lower levels of residual monomer.

SUMMARY OF THE INVENTION

The present invention relates to a cationic water-soluble polyelectrolyte compositions, especially surfactant-based conditioning or cleansing compositions comprising, a cationic, water-soluble polyelectrolyte having a charge density>0.001 meq/g and less than 4 meq/g, and a solution viscosity between 10 mPas to 3000 mPas at a concentration of 1.5 wt % polymer as measured by standard viscosity measurements in which the polymer is measured in deionized water using a Brookfield viscometer, spindle #4, at 30 rpm. The cationic, water-soluble polyelectrolyte is synthesized by adiabatic gel polymerization processes or as water-in-water dispersions and consist of copolymers and terpolymers of (meth)acrylamide and cationic monomers based on (meth) acrylamide, and/or hydrolysis stable cationic monomers, and/ or monomers based on cationic(meth)acrylic acid esters. The cationic, water-soluble polyelectrolyte demonstrates:

(1) an enhanced deposition of silicone or conditioning agent to hair and keratinous substrates, textile substrates, and hard-surface substrates, from conditioning shampoo formulations or cleansing formulations, as well as a more targeted deposition of silicone or conditioning agent to damaged areas of the substrate or more uniform deposition of silicone or conditioning agent across the substrate, e.g., the length of the hair fiber, while maintaining less "stringy" rheology in the formulation, in contrast to the elastic rheology associated with higher MW cationic water-soluble polyelectrolytes in the prior art;

(2) an enhanced deposition of antidandruff actives such as zinc to the scalp or deposition of other antimicrobial agents to the skin or hard-surface substrates from antimicrobial formulations, and improved aesthetic aspects of the cleansing experience, such as lather development and texture, when compared to the higher MW cationic water-soluble polyelectrolytes in the prior art; and (3) an enhanced solubility, clarity, and improved deposition profiles in surfactant based systems when compared to the higher MW cationic water-soluble polyelectrolytes in the prior art.

(4) lower residual monomer levels when compared with other synthetic polyelectrolytepolymers in the prior art.

In the present invention, it has also been found that compositions comprising a combination of cationic polymers selected from (A) cationically water-soluble synthetic polyelectrolyte polymers, especially cationic acrylamide polymers having a cationic charge density at pH7 of greater than 0.001 meq per gram and less than 4 meq/g and (B) one or more cationic polymers selected from non-cellulosic cationically-modified polysaccharides, and an acid or base component produces a composition that is (1) both readily dispersible in aqueous formulations without pH adjustment and without lumping, (2) the resulting aqueous composition or polymer blend composition can be formulated into surfactant compositions, such as cleansing compositions to produce formulations which demonstrate enhanced deposition of dispersed phase components, such as silicone, zinc pyrithione, fragrance, colorant, and other active components, onto substrates such as hair, skin, fabrics, and (3) the formulations show reduced stringiness and improved aesthetics, such as foaming and lather generation.

The enhanced deposition of the dispersed phase materials is independent of the particle size of the dispersed phase material.

The aqueous solution viscosity of cationic acrylamide polymers correlates with the molecular weight of the cationic acrylamide. Once the viscosity of a cationic acrylamide polymer is reduced to below 200 mPas (@ 1 wt % polymer solids; spindle #1, 10 rpm, @ 20° C., in 10% NaCl the "stringy" rheology that the cationic acrylamide polymer imparts to surfactant based formulations is significantly reduced.

The blending of cationic polygalactomannans at a ratio of between about 0.001-10 cationic acrylamide/wt galactomannan polymer, and acids such as citric acid, fumaric acid, adipic acid, and other neutralizing acids and bases, such as sodium bicarbonate, produces a dry powder composition that readily disperses in water to produce a smooth aqueous polymer solution. This composition in either aqueous polymer solution or the dry powder composition form can be added directly to a personal care or household care formulation, such as a surfactant-based formulation, to produce a composition which demonstrates improved silicone deposition but reduced stringiness, and improved lathering and foaming performance. This polymer solution or the dry powder composition can also find use in textile applications, oil recovery applications, paper applications, and coating applications.

This composition is of utility in formulating cosmetic or personal care compositions, in particular cleansing compositions, such as body wash, shampoo formulations and in addition, conditioner compositions. This composition is also of utility in formulating household care compositions, textile care compositions, paper compositions, paper coating compositions, and coating compositions.

An advantage of the use of this composition over the individual polymers is an improved deposition of dispersed phases from surfactant based systems and an improved conditioning performance that the composition imparts, especially in personal care and household care compositions, without the negative effects of undesirable "stringy" rheology, and with improved foaming and lather performance. An additional advantage of blending cationic water-soluble synthetic polyelectrolytes of a certain molecular weight and charge density with non-cellulosic cationic polysaccharide polymers of a certain molecular weight and charge density, creates a composition that is both readily dispersible in aqueous formulations without pH adjustment and without lumping. The composition does not impart elastic, "stringy" rheology to surfactant-based formulations. In contrast, higher MW cationic acrylamide polymers typically dissolve to impart a "stringy" rheology to formulations. In contrast, the compositions of the present invention deliver formulations with more desirable rheology, and reduced stringiness.

The compositions of the present invention can be formulated into surfactant compositions, such as cleansing compositions to produce formulations which impart improved deposition of active components, while having reduced stringiness and improved aesthetics, such as foaming and lather generation. The compositions of the present invention can also be formulated into conditioning formulations such as hair conditioners, to impart smoothness and reduced tangling during the wet and dry state combing of hair.

Surfactant-based conditioning or cleansing compositions comprising the cationic, water-soluble polyelectrolytes of the present invention and combinations of these cationic, water-soluble polyelectrolyte polymers with non-cellulosic cationic polysaccharides or their derivatives have been shown to deliver improved uniformity or targeted delivery of silicone deposition along the hair fiber on all hair types, including damaged hair or bleached hair, delivering improved lubricity or softness to hair, as measured by dry comb and friction measurements, improved combing performance and improved aesthetic aspects of the cleansing experience, such as lather development and texture when delivered from silicone and nonsilicone cleansing compositions, and enhanced delivery of antidandruff agents such as zinc pyrithione and zinc carbonate to artificial skin (as a model for the scalp), while maintaining less "stringy" rheology, in contrast to the elastic rheology associated with higher MW cationic water-soluble polyelectrolytes in the prior art.

It has also been found that application of combinations of crosslinking agents based on borate salts, aluminum salts, copper, iron, calcium, and sodium salts, glyoxal, and metal salts based on titanium and zirconium, as disclosed in US Publication Nos. 2008-0112907 A1 and 2008-0112906 A1, the disclosures of which are incorporated herein by reference, with polyols or polysaccharide polymers applied as a surface coating to the polymer combination of the cationic, water-soluble polyelectrolyte polymers with non-cellulosic cationic polysaccharides or their derivatives, improves the dispersibility and dissolution performance of the compositions of the invention.

These compositions are also expected to deliver improved deposition of other benefiting active materials, such as colors or dyeing agents, antidandruff agent such as selenium and salicylic acid, fragrance, antimicrobial materials, UV protector, sun blockers, hair growth agents etc., onto the scalp, the hair, and onto hair, skin, other keratinous substrates, textile substrates, and hard-surface substrates.

DETAILED DESCRIPTION OF THE INVENTION

Figure 1:
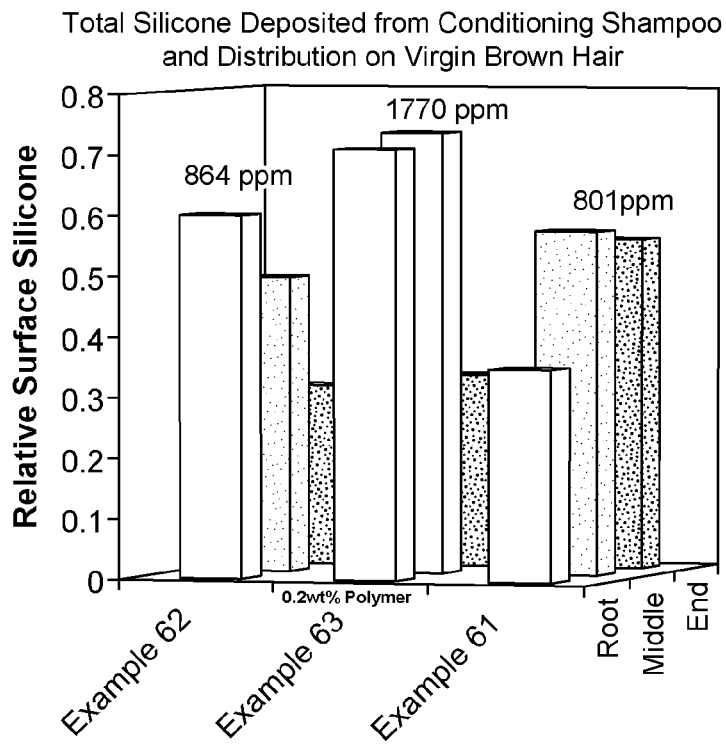
FIG. 1 is a graph showing total silicone deposited from conditioning shampoo and distribution on virgin brown hair.

The surfactant based compositions of the present invention will include a cationic water-soluble polyelectrolyte in combination with a surfactant and an active ingredient typically included in either a household care composition, textile care composition or personal care composition. In a second embodiment of the present invention, the surfactant based system will further include, in addition to the cationic water soluble polyelectrolyte and surfactant, a cationic polysaccharide wherein the composition is particularly effective in increasing the deposition of a dispersed phase of the composition.

The cationic water-soluble polyelectrolyte is formed from (1) copolymers of (meth)acrylamide and cationic monomers based on (meth)acrylamide, and/or hydrolysis stable cationic monomers, (2) terpolymers of (meth)acrylamide, monomers based on cationic(meth)acrylic acid esters, and monomers based on (meth)acrylamide, and/or hydrolysis stable cationic monomers. Throughout this application, the term (meth)acrylamide defines methylacrylamide and acrylamide, and (meth) acrylic acid defines acrylic acid and methacrylic acid.

The cationic water-soluble synthetic polyelectrolytes have a total charge density from about 0.001 to 4 meq/g, preferably about 1.0-2.5 meq/g, and more preferably about 1.5-2.2 meq/g, and their solution viscosity, measured as 1% solution in deionized water is 10 to 3000 mPas, preferably 80 to 2000 mPas, and more preferably 90 to 1500 mPas. Further, the molecular weight as measured by size exclusion chromatography is from about 500,000 to 2 million and generally about 1 million as explained hereinafter.

Cationic monomers based on (meth)acrylic acid esters include, cationized esters of the (meth)acrylic acid containing a quaternized N atom. Preferably there are used quaternized dialkylaminoalkyl(meth)acrylates with $C_1$ to in the alkyl and alkylene groups, especially ammonium salts of dimethylaminomethyl(meth)acrylate, dimethylaminoethyl(meth)acrylate, dimethylaminopropyl(meth)acrylate, diethylaminomethyl(meth)acrylate, diethylaminoethyl(meth)acrylate and diethylaminopropyl(meth)acrylate quaternized with methyl chloride. Particularly preferred is dimethylaminoethyl acrylate, which is quaternized with an alkyl halide, especially with methyl chloride or benzyl chloride or dimethyl sulfate (ADAME-Quat).

Cationic monomers based on (meth)acrylamides include quaternized dialkylaminoalkyl(meth)acrylamides with $C_1$ to $C_3$ in the alkyl and alkylene groups. Particularly preferred is dimethylaminopropylacrylamide, which is quaternized with an alkyl halide, especially methyl chloride or benzyl chloride or dimethyl sulfate.

Hydrolysis-stable cationic monomers can be, in addition to the dialkylaminoalkyl(meth)acrylamides described in the foregoing, all monomers that can be regarded as stable to the OECD hydrolysis test. Examples are diallyldimethylammonium chloride or water-soluble, cationic styrene derivatives.

Particularly preferred as cationic polyelectrolytes according to the invention are terpolymers of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). Another preferred polyelectrolyte is formed from acrylamide and acrylamidopropyltrimethylammonium chloride with a charge density of 1.0-3.0 meg/g.

The polyelectrolytes can be synthesized by known methods, such as emulsion, solution, gel and suspension polymerization, preferably gel and solution polymerization. By controlling the method of polymerization, the concentration of unreacted residual monomer in the end product can be controlled. Generally, it is desirable to have residual monomers present in the polyelectrolyte of less than about 0.04%, preferably less than 0.02%, and most preferably less than 0.01%. We have found that additional post-polymerization processing steps further reduce the unreacted residual monomer in the polyelectrolyte product to less than about 0.005%.

Preferably such polyelectrolytes are synthesized by mixing the combination of the cationic monomers based on (meth) acrylic acid esters and monomers based on (meth)acrylamides and/or hydrolysis-stable cationic monomers and (meth)acrylamide and initiating the polymerization. During the polymerization a solid gel is formed from the monomer solution, and is subsequently crushed, dried and ground.

The polymerization is preferably carried out as an adiabatic polymerization, and it can be initiated either with a redox system or with a photoinitiator. Moreover, a combination of both initiation methods is possible. The redox initiator system is composed of at least two components—an organic or inorganic oxidizing agent and an organic or inorganic reducing agent. In many cases, compounds containing peroxide units are used for this purpose. Examples are inorganic peroxides such as alkali metal and ammonium persulfate, alkali metal and ammonium perphosphates, hydrogen peroxide and its salts, especially sodium peroxide and barium peroxide, or organic peroxides such as benzoyl peroxide and butyl hydroperoxide, or per acids such as peracetic acid. In addition, however, other oxidizing agents can also be used, such as potassium permanganate, sodium and potassium chlorate, potassium dichromate, etc. As reducing agents there can be used sulfur-containing compounds such as sulfites, thiosulfates, sulfonic acid and organic thiols such as ethylmercaptan and 2-hydroxy-ethanethiol, 2-mercaptoethylammonium chloride, thioglycolic acids and others. In addition, there can also be used ascorbic acid and low-valency metal salts, preferably copper (I), manganese (II) and iron (II) salts. Phosphorus compounds can also be used, such as sodium hypophosphite. In the case of photopolymerization, the reaction is initiated with UV light, which causes decomposition of the initiator. As initiators there can be used benzoin and benzoin derivatives, such as benzoin ether, benzyl and its derivatives, such as benzyl ketals, acryldiazonium salts, azo initiators such as 2,2"-azobis(isobutylronitrile) and 2,2"-azobis(2-amidinopropane)hydrochloride or acetophenone derivatives. The quantity of the oxidizing and reducing components can range from 0.00005 to 0.5 weight percent, preferably from 0.001 to 0.1 weight percent, preferably from 0.001 to 0.1 weight percent relative to the monomer solution. For photoinitiators it can range from 0.001 to 0.1 weight percent, preferably 0.01 to 0.08 weight percent.

The polymerization is carried out batch-wise in aqueous solution in a polymerization vessel or continuously on an endless belt, as described, for example, in German Patent 3544770. This step is introduced herewith as the reference step, and is incorporated as part of the disclosure. The process is initiated at a temperature of between −20 and 50° C., preferably between −10 and 10° C., and is carried out at atmospheric pressure without external heat supply. Because of the heat of polymerization, a maximum final temperature of 50 to 150° C. is reached, depending on the content of polymerizable substance.

On completion of polymerization, the polymerized product obtained in the form of a gel is crushed.

The crushed gel is now dried batch-wise in a circulating-air drying oven at 70 to 150° C., preferably at 80 to 130° C. Drying can be achieved continuously in the same temperature ranges on a belt dryer or in a fluidized-bed dryer.

The composition may include 0.001 to 50 wt %, preferably 0.005 to 25 wt %, and particularly preferably 0.05 to 10 wt % of the cationic, low molecular weight polyelectrolyte.

The cationic water-soluble synthetic polyelectrolyte of use in the present invention is one component of the composition. A second component of the composition is a surfactant. An optional component is a compatible solvent which may also be used in the cleansing composition that can be either a single solvent or a blend of solvents.

Examples of the surfactants are anionic, nonionic, zwitterionic, cationic or amphoteric type of surfactants, and blends thereof. The anionic, nonionic, zwitterionic, cationic, or amphoteric surfactant can be soluble or insoluble in the present invention and (when used) is present in the composition in the amount of from 0.01 to about 50 wt % by weight of the composition. Synthetic anionic surfactants include alkyl and alkyl ether sulfates, phosphate esters, and other anionic surfactants commonly used in personal care and household formulations.

Nonionic surfactants, can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Nonionic surfactants such as those marketed under the trade name Surfynol®, available from Air Products and Chemicals, Inc. are also useful in this invention.

Zwitterionic surfactants are exemplified by those which can be broadly described as derivative of aliphatic quaternary ammonium, phosphonium, and sulfonium compounds in which the aliphatic radicals can be straight or branched chain, and wherein one of the aliphatic substituents contains from about 8 to about 18 carbon atoms and one contains as anionic water-solubilizing group, e.g., carboxy, sulfonate, sulfate, phosphate, or phosphonate.

Examples of amphoteric surfactants which can be used in the vehicle systems of the cleansing composition of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

According to the present invention, the solvent used in the system should be compatible with the other components of the cleansing composition. Examples of the solvents that may be used in the present invention are water, water-lower alkanols mixtures, and polyhydric alcohols having from 3 to 6 carbon atoms and from 2 to 6 hydroxyl groups. Preferred solvents are water, propylene glycol, water-glycerine, sorbitol-water, and water-ethanol. The solvent (when used) in the present invention is present in the composition at a level of from about 0.1% to 99% by weight of the composition.

Other conditioning ingredients and nonconditioning active ingredients or benefiting agents can also be included. The dissolved synthetic polyelectrolyte acts as a conditioner and deposition agent. An example of this is the use of the polymer in an aqueous solution as a conditioner for hair or skin conditioning, as a fabric conditioner, or as an antimicrobial agent. However, when an additional active ingredient or benefit agent is needed, it must provide some benefit to the user or the user's body. Generally, the compositions will include one or more conditioning and nonconditioning active ingredients as discussed below.

In accordance with the present invention, the personal care composition, household care composition or institutional care composition may be a cleansing composition. When the cleansing composition is a personal care product that contains at least one active personal care ingredient or benefit agent, the personal care active ingredient or benefit agent may include, but is not limited to, analgesics, anesthetics, antibiotic agents, antifungal agents, antiseptic agents, antidandruff agents, antibacterial agents, vitamins, hormones, anti-diarrhea agents, corticosteroids, anti-inflammatory agents, vasodilators, kerolytic agents, dry-eye compositions, wound-healing agents, anti-infection agents, UV absorbers, as well as solvents, diluents, adjuvants and other ingredients such as water, ethyl alcohol, isopropyl alcohol, propylene glycol, higher alcohols, glycerine, sorbitol, mineral oil, preservatives, functional polymers, surfactants, propellants, fragrances, essential oils, jojoba oil, meadowfoam seed oil or other seed oils, silicone oils or polymers, emollients, and viscosifying agents.

Personal care compositions include hair care, skin care, sun care, nail care, and oral care compositions. Examples of active personal care ingredients or benefit agents that may suitably be included, but not limited to, in the personal care products according to the present invention are as follows:

1) Perfumes, which give rise to an olfactory response in the form of a fragrance and deodorant perfumes which in addition to providing a fragrance response can also reduce body malodor;

2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin;

3) Emollients, such as isopropylmyristate, silicone materials, mineral oils, seed oils, and vegetable oils which give rise to a tactile response in the form of an increase in skin lubricity;

4) Deodorants other than perfumes, whose function is to reduce the level of or eliminate micro flora at the skin surface, especially those responsible for the development of body malodor. Precursors of deodorants other than perfume can also be used;

5) Antiperspirant actives, whose function is to reduce or eliminate the appearance of perspiration at the skin surface;

6) Moisturizing agents, that keep the skin moist by either adding moisture or preventing from evaporating from the skin;

7) Sunscreen active ingredients that protect the skin and hair from UV and other harmful light rays from the sun. In accordance with this invention a therapeutically effective amount will normally be from 0.01 to 10% by weight, preferable 0.1 to 5% by weight of the composition;

8) Hair treatment agents, that condition the hair, cleanse the hair, detangles hair, acts as styling agent, volumizing and gloss agents, color retention agent, anti-dandruff agent, hair growth promoters, hair dyes and pigments, hair perfumes, hair relaxer, hair bleaching agent, hair moisturizer, hair oil treatment agent, and antifrizzing agent; and 9) Oral care agents, such as dentifrices and mouth washes, that clean, whiten, deodorize and protect the teeth and gum.

In accordance with the present invention, when the cleansing composition is a household care composition, this household care composition includes a cationic water-soluble synthetic polyelectrolyte compositions and at least one active household care ingredient or benefit agent. The household care active ingredient or benefit agent must provide some benefit to the user. Examples of active ingredients that may suitably be included, but not limited to, according to the present invention are as follows:

1) Perfumes, which give rise to an olfactory response in the form of a fragrance and deodorant perfumes which in addition to providing a fragrance response can also reduce odor;

2) Insect repellent agent whose function is to keep insects from a particular area or attacking skin;

3) Bubble generating agent, such as surfactant that generates foam or lather;

4) Pet deodorizer or insecticides such as pyrethrins that reduces pet odor;

5) Pet shampoo agents and actives, whose function is to remove dirt, foreign material and germs from the skin and hair surfaces;

6) Industrial grade bar, shower gel, and liquid soap actives that remove germs, dirt, grease and oil from skin, sanitizes skin, and conditions the skin;

7) Disinfecting ingredients that kill or prevent growth of germs in a house or public facility;

8) A laundry softener active, which reduces static and makes fabric feel softer;

9) Laundry or detergent or fabric softener ingredients that reduce color loss during the wash, rinse, and drying cycle of fabric care;

10) Toilet bowl cleaning agents, which remove stains, kills germs, and deodorizes;

11) Laundry prespotter actives which helps in removing stains from clothes; and

12) Fabric sizing agent which enhances appearance of the fabric.

The above lists of personal care and household care active ingredients or benefit agents are only examples and are not complete lists of active ingredients that can be used. Other ingredients that are used in these types of products are well known in the industry. In addition to the above ingredients conventionally used, the composition according to the present invention can optionally also include ingredients such as a colorant, preservative, antioxidant, nutritional supplements, alpha or beta hydroxy acid, activity enhancer, emulsifiers, functional polymers, viscosifying agents (such as salts, i.e., NaCl, $NH_4Cl$, and KCl, water-soluble polymers, i.e., hydroxyethylcellulose and hydroxypropylmethylcellulose, and fatty alcohols, i.e., cetyl alcohol), alcohols having 1-6 carbons, fats or fatty compounds, antimicrobial compound, zinc pyrithione, silicone material, hydrocarbon polymer, emollients, oils, surfactants, medicaments, flavors, fragrances, suspending agents, and mixtures thereof.

In accordance with the invention, the silicone materials which can be used are polyorganosiloxanes that can be in the form of polymers, oligomers, oils, waxes, resins, or gums or polyorganosiloxane polyether copolyols, amodimethicones, cationic polydimethylsiloxane materials and any other silicone material that is used in personal care compositions, household care compositions or institutional care compositions. The cationic water-soluble synthetic polyelectrolyte compositions of use in this invention can be used as conditioning agents in 2-in-1 shampoos, conditioners, body lotions, sunscreens, antifrizz and hair styling formulations. The cationic water-soluble synthetic polyelectrolyte compositions of use in this invention can also be used to improve hair volume, manageability, hair repair, or color retention, skin moisturization and moisture retention, fragrance retention, sunscreen longevity on hair, skin, and fabrics, flavor enhancement and antimicrobial performance in oral care applications, and improve fabric abrasion resistance and colorfastness in household applications.

The composition can be formulated based on the end use product. Different formulations may require different orders of addition in order to achieve the desired end product with desired characteristics.

In accordance with this invention, the conditioning benefits of cationic water-soluble synthetic polyelectrolyte are demonstrated as conditioning agents in personal care compositions such as hair care and skin care compositions. Performance is also expected in oral care compositions, such as toothpastes, oral rinses, anticaries mouth rinses, and antimicrobial mouthwashes as well as household care compositions, such as laundry cleaner and softener products for textile substrates and hard surface cleaner products.

In accordance with the present invention, the functional system substrate is defined as a material that is related to personal care and household care applications. In personal care, the substrate can be skin, hair, teeth, and mucous membranes. In household care products, the substrate can be hard surfaces such as metals, marbles, ceramics, granite, wood, hard plastics, and wall boards or soft surfaces such as textiles and fabrics.

This formulation is particularly beneficial as a deposition aid for dispersed phase compositions, such as the personal care ingredients previously listed, for use on damaged hair or onto the scalp or skin. By incorporating a formulation including a synthetic cationic polyelectrolyte of the present invention in combination with a dispersed phase composition such as a silicone oil or jojoba oil, meadowfoam seed oil, or antidandruff actives such as zinc pyrithione, the amount of oil deposited on the damaged hair and scalp and the amount of antidandruff active deposited onto the scalp is increased. Such a composition will also include a surfactant and suspending agent, which maintains the oil or other dispersed phase suspended in the composition as droplets or particles. When diluted during use these particles or droplets deposit onto the substrate. The formulation of the present invention with the synthetic cationic polyelectrolyte can increase the deposition of an oil on damaged hair from 100 ppm to 1000 ppm.

One particular embodiment of the present invention will further include a noncellulosic cationically modified polysaccharide. The combination of the synthetic polyelectrolyte with a noncellulosic cationic modified polysaccharide further improves deposition of conditioning agents and active ingredients.

In this embodiment, the composition is a combination of the cationic, water-soluble, synthetic polyelectrolytes and the non-cellulosic cationically modified polysaccharides. The non-cellulosic cationically modified polysaccharides may contain varying amounts of protein as part of their composition. In accordance with the present invention, non-cellulosic cationically modified polysaccharides, and more particularly polygalactomannan compositions or polyglucomannan compositions, that contain quaternary ammonium groups, covalently attached to the polysaccharide backbone, have the cationic degree of substitution (DS) having a lower limit of about 0.0005 and an upper limit of about 3.0. Preferably, the lower limit of the cationic DS is 0.001, and more preferably 0.002 and even more preferably 0.01. Preferably, the upper limit of the cationic DS is 3.0, more preferably 1.0, and even more preferably 0.35. The cationic polygalactomannan or derivative thereof of the present invention generally has a weight average molecular weight (MW) with a lower limit of about 10,000 and an upper limit of about 2,000,000. Preferably, the lower limit of the molecular weight is about 100,000, and more preferably about 200,000. Preferably, the upper limit of the molecular weight is about 1,500,000, more preferably about 1,000,000.

In accordance with present invention, the non-cellulosic cationically modified polysaccharide, and more preferably the cationic polygalactomannan or cationic derivatized polygalactomannan can have a crosslinker present, such as boron, glyoxal, or other treatment that renders the non-cellulosic cationically modified polysaccharide readily dispersible without clumping in water. The crosslinker content can be less than 5 wt % per gram of non-cellulosic cationically modified polysaccharide, and preferably less than 1 wt %. The crosslinker may also be of a type that can form irreversible covalent crosslinks with the polymers of the invention, producing a product with more swelling performance in aqueous systems.

The polygalactomannan gum from which the non-cellulosic cationically modified polysaccharide of the present invention is derived is selected from the group consisting of guar, locust bean, tara gum, honey locust, cassia, and flame tree. Other non-cellulosic polysaccharides useful in the present invention include xanthan gum, gellan gum, welan gum, rhamsan gum, konjac mannan, gum arabic, soy polysaccharide, xylofructose gums and tamarind gum.

The cationic functionalities of the non-cellulosic cationically modified polysaccharide can be added to the backbone by known methods. For example, the non-cellulosic polysaccharide, such as polygalactomannan can be reacted for a sufficient time and at a sufficient temperature with a first quaternary ammonium alkylating reagent, such as 3-chloro-2-hydroxypropyltrimethylammonium chloride, and 2,3-epoxy-propyltrimethylammonium chloride. Preferred examples include a combination of two glycidyltrialkylammonium salts or 3-halo-2-hydroxypropyltrialkylammonium salts where the first quaternary ammonium reagent is glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding bromides and iodides; and quaternary ammonium compounds such as halides of imidazoline ring containing compounds.

The non-cellulosic cationically modified polysaccharide may also contain other substituent groups such as nonionic substituents, i.e., hydroxyalkyl wherein the alkyl represents a straight or branched hydrocarbon moiety having 1 to 30 carbon atoms (e.g., hydroxymethyl hydroxyethyl, hydroxypropyl, hydroxybutyl), alkyl, aralkyl, or aryl groups wherein the alkyl represents a straight or branched hydrocarbon moiety having 1 to 30 carbon atoms, or anionic substituents, such as carboxymethyl groups, sulfonic acid groups, or phosphonic acid groups are optional. These optional substituents are linked to the non-cellulosic polysaccharide by the reaction with reagents such as for example (1) alkylene oxides (e.g., ethylene oxide, propylene oxide, butylene oxide) to obtain hydroxyethyl groups, hydroxypropyl groups, or hydroxybutyl groups, or with (2) chloromethyl acetic acid to obtain a carboxymethyl group, or with (3) chloroethylsulfonic acid to obtain a sulfonic acid group, or with (4) chloroethylphosphonic acid to obtain a phosphonic acid group. The process for preparing a derivatized non-cellulosic polysaccharide is well known in the art. The non-cellulosic cationically modified polysaccharide may also contain a mixture of one or more other substituent groups such as nonionic, anionic and cationic substituents.

In accordance with the present invention, examples of functional polymers that can be used in blends with the non-cellulosic cationically modified polysaccharide of this invention include water-soluble polymers such as acrylic acid homopolymers such as Carbopol® product and anionic and amphoteric acrylic acid copolymers, vinylpyrrolidone homopolymers and cationic vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydroxypropylcellulose; acrylamide homopolymers and cationic, amphoteric, and hydrophobic acrylamide copolymers, polyethylene glycol polymers and copolymers, hydrophobic polyethers, hydrophobic polyetheracetals, hydrophobically-modified polyetherurethanes and other polymers referred to as associative polymers, hydrophobic cellulosic polymers, polyethyleneoxide-propylene oxide copolymers, and nonionic, anionic, hydrophobic, amphoteric, and cationic polysaccharides such as xanthan, chitosan, carboxymethyl guar, alginates, gum arabic, nonionic, cationic, anionic, and amphoteric guar polymers such as hydroxypropyl guar, hydrophobic guar polymers, carboxymethyl guar hydroxypropyltrimethylammonium chloride, guar hydroxypropyltrimethylammonium chloride, and hydroxypropyl guar hydroxypropyltrimethylammonium chloride.

The ratio of synthetic polyelectrolyte to noncellulose polysaccharide will range from 99:1 polysaccharide:synthetic polyelectrolyte, to 1:99 polysaccharide:synthetic polyelectrolyte by weight. Generally, the combination of the polysaccharide and synthetic polyelectrolyte will be from 5 to 30 wt % synthetic polyelectrolyte and 95 to 70 wt % polysaccharide. This combination can be blended with the surfactants, solvents and active ingredients previously discussed to formulate improved household care compositions or personal care compositions.

The composition having the synthetic cationic polyelectrolyte and the cationic polysaccharide is particularly suited for the deposition of oily components upon substrates, other than damaged hair. For example, using this combination with an oily composition can increase the deposition of an oil phase from about 500 ppm to about 1200-1500 ppm. This allows the formulation to use less oil because more of the oil in the formulation is actually deposited.

This composition can incorporate any of the conditioning oils or other conditioning agents previously discussed and, of course, can be utilized with any of the non-conditioning benefit agents previously discussed, to formulate either a cleaning composition, a personal care product composition, a household care product composition, or an institutional care product composition, as previously discussed.

For a more detailed understanding of the invention, reference can be made to the following examples which are intended as further illustrations of the invention but are not to be construed in a limiting sense. All parts and percentages are by weight unless stated otherwise.

EXAMPLES

In order to achieve improved aesthetic performance, including reduced stringiness, and improved deposition performance, a series of lower molecular weight cationic polyacrylamide polymers were prepared through adiabatic gel polymerization procedures as set forth in U.S. Pat. No. 7,375,173, previously incorporated herein by reference.

Method of Preparation of Blends

The following general method was used for preparation of the blend material in Examples 10, 11, and 12 in Table 1. This same method was used for preparation of all blend materials described in the Examples section.

The cationic guar polymers were used as received. The cation synthetic polyelectrolytes of the invention were milled through a Netzsch Condux CUM 150 Universal Mill configured with a 0.2 Micron Connidur screen and Blast Rotor operating at 8000 RPMs mill to yield a powder between (50-60 μm). The ground form of the cationic polyacrylamide had a reduced content of the residual acrylamide monomer (12 ppm) vs the original unground sample (183 ppm) as measured by the liquid chromatography method as described in the Methods section.

The dry polymer powders were then blended mechanically using a ribbon blender or a Long Roll Jar Mill. A solution of 25-50 wt %) aqueous citric acid solution was sprayed onto the blended mixture using an analog spraying blender (Cuisinart 14 cup food processor, Tuthill pump, spray gun, and a scale balance). To reach the desired moisture (6-8% moisture) the blends were dried using a fluid bed dryer.

The blends were tested for homogeneity using standard NMR methods.

Examples 1-14

In a shampoo formulation containing 12% sodium lauryl ether sulfate/2% cocamidopropyl betaine surfactant system blends, the shampoo formulations containing the high molecular weight, higher viscosity cationic acrylamide polymers, as shown in Examples 2-3 in Table 1, contained residual undissolved gels even after long dissolution times.

The solubility of the lower molecular weight cationic acrylamide polymer prepared by the adiabatic gel polymerization process was significantly improved as shown by the absence of gels and lack of haze (higher clarity) in the resulting shampoo formulation for the polymers of the invention in Examples 8 and 9. The polymers of the invention in Examples 8 and 9 show improved solubility and clarity in shampoo formulations, even when compared with lower MW cationic acrylamide polymers prepared by solvent polymerization (Example 5) or emulsion polymerization processes (Example 4).

It is important to note that the shampoo in Example 5 contained undissolved gels even after long dissolution times, despite the low aqueous viscosity or molecular weight for this polymer. It has been determined that this polymer was prepared through a solvent polymerization process, not the adiabatic gel polymerization process used for the polymers in Examples 1-3, and 6-9.

The target molecular weight for improved solubility in the shampoo and for improved performance was identified as polymer viscosity in Examples 8 and 9. The polymers of Examples 8 and 9 have similar viscosities as polymers in Examples 4 and 5 in Table 1, however, as shown in Tables 1 and 2, the polymers of the invention in Examples 8 and 9 have better clarity and solubility in surfactant-based formulations such as shampoo and bodywash formulas, such as those shown in Tables 1 and 2.

Polymer solution viscosity data in Table 1 are used for comparison of polymer molecular weight. As mentioned above, although the polymers of Examples 4 and 5 have similar viscosity as the polymers of the invention in Examples 8 and 9, they differ from the polymers of the invention in their solubility in surfactant based systems as shown by the shampoo clarity values, expressed as % Transmittance (% T) @ 600 nm in Tables 1 and 2.

Additional differences between the polymer of the invention and the polymer of Example 5 have been noted in measurements of particle shape and spherical particle content that further differentiate these polymers. By using a PartAn 2001 L, a photo-optical image analyzing system, the non-spherical parameter (NSP), a shape factor of these polymer particles was measured. These measurements showed for the particles of the polymer of Example 5 a deviation of the NSP from an ideal spherical shape of approx. 14% and for the polymers of the invention (Example 7 and 9) a deviation of approximately 76%.

The gap reading at string break as measured on a rheometer for each shampoo, is used as a measure of the degree of "stringy" rheology for each shampoo. On comparison of the gap readings for Examples 5-12 in Table 1, it can be concluded that the gap readings, and associated "stringiness" of the shampoo, were greater for the highest molecular weight cationic acrylamide in example 6 and lower for the lower viscosity cationic acrylamides in examples 8 and 9. The "stringy" character of cationic guar blends with these acrylamides also decreases as the molecular weight of the cationic acrylamide decreases, in the order Example 10>11>12. Polymers of the invention in Examples 13 and 14 as described in U.S. Pat. No. 7,375,173 in Table 1 also deliver low string values in the shampoo formulation used in Table 1, for polymers of both low and medium MW. These polymers gave clear aqueous solutions and delivered opaque shampoos in this formula.

The polymers of the invention in examples 9-12 in table 1 also have very low unreacted acrylamide monomer present relative to the comparative Examples 1-7.

| EX. | Polymer[1] | Source: Cationic acrylamide[2] Polymer | Mw (SEC method) | meq/gram charge density@ pH5/pH7 | 1.5% Polymer Viscosity/cps 30 rpm, spindle 4 | Shampoo Viscosity[3]/cps 30 rpm, spindle 4 | Shampoo Phase Behavior | Gap Reading at String Break[4] | Stringiness Rank of Shampoo | Unreacted acrylamide monomer/ppm |
|---|---|---|---|---|---|---|---|---|---|---|
| 1 | APTAC-Acm | Ashland Inc. | 1.04E6 | 1 | 2960 | 5100 | Clear, no gels | | | 193 |
| 2 | APTAC-AcM | Ashland Inc | | 2.05 | 3300 | 6900 | Large hazy gels at bottom of shampoo | | | 464 |

-continued

| EX. | Polymer[1] | Source: Cationic acrylamide[2] Polymer | Mw (SEC method) | meq/ gram charge density@ pH5/pH7 | 1.5% Polymer Viscosity/ cps 30 rpm, spindle 4 | Shampoo Viscosity[3]/ cps 30 rpm, spindle 4 | Shampoo Phase Behavior | Gap Reading at String Break[4] | Stringiness Rank of Shampoo | Unreacted acrylamide monomer/ ppm |
|---|---|---|---|---|---|---|---|---|---|---|
| 3 | APTAC-AcM | Ashland Inc. | 1.18E6 | 2. | 4700 | 5960 | Large clear gels at bottom of shampoo | | | 245 |
| 4 | MAPTAC-AcM | Kemira | | 0.5 | 1720 | 1840 | Hazy, no gels apparent | | | 36 |
| 5 | APTAC-AcM | Ciba | 1.21E6 | 1.98 | 1360 | 5980 | Slightly hazy Required extended mix time* to reduce/ eliminate gels. Several gels found at bottom of shampoo * ~8 hrs at 300 rpm | | 4 | 311 |
| 6 | APTAC-Acm | Developmental | 1.41E6 | — | 2800 | | Large gels | 6335 | 1 most | |
| 7 | APTAC-Acm | Developmental | 1.18E6 | — | 1800 | | Some gels | 6306 | 2 | |
| 8 | APTAC-Acm | Polymer of invention | 1.14E6 | 1.88 | 1400 | | no gels | 6183 | 3 | |
| 9 | APTAC-Acm | Polymer of Invention | 1.14E6 | 1.92 | 800 | | no gels | 5976 | 4 | 4 |
| 10 | Blend cationic guar[5]/Polymer Example 2 | Polymer of Example 2 | | | | | no gels | 5855 | 5 | 2 |
| 11 | Blend cationic guar/Polymer Example 8 | Polymer of invention | 1.01E6 | 1.14 | | | no gels | 5803 | 6 | 2 |
| 12 | Blend cationic guar/Polymer Example 9 | Polymer of invention | 1.01E6 | | | | no gels | 5706 | 7 low | 2 |
| 13 | APTAC-AETAC-Acm | Polymer of Invention | | 2.44 | 3600@ 2% | 3820 | Opaque | 5165 | 9 lowest | |
| 14 | APTAC-AETAC-Acm | Polymer of Invention | | 2.44 | 3600@ 2% | 4360 | Opaque | 5465 | 8 lower | |

[1]APTAC-AcM = acrylamidopropyltrimethyl ammonium chloride/acrylamide copolymer, MAPTAC = methacrylamidopropyl trimethylammonium chloride
[2]Examples 1-3: Praestol ® offered by Ashland Inc., Example 4: Callaway ® offered by Kemira, Example 5: Salcare ® SC60 offered by Ciba
[3]12% sodium laureth sulfate(SLES)(2EO)/2% cocamidopropyl betaine, CAPB; 1% Sodium Chloride; 0.2 wt % polymer
[4]"Stringiness" measured: AR-G2 Rheometer from TA Instruments. Parallel plate geometry, 60 mm diameter. Pull at 10 u/min
[5]N-Hance ® BF13 cationic guar offered by Ashland Inc, Ashland Aqualon Functional Ingredients Group,, also in Examples 11, 12.

TABLE 2

Shampoo Clarity as % Transmittance @ 600 nm

| Example | Polymer[6] | Cationic Acrylamide Polymer or Blend w/ Cationic Guar | meq/gram charge density | 1.5% Polymer Viscosity/cps 30 rpm, spindle 4 | 12% SLES/ 2% CAPB[7] Shampoo % T @600 nm | % T@600 nm APG Surfactant shampoo[8] | % T@600 nm ALS/ALES Surfactant shampoo[9] | VISC./CPS & APPEARANCE ALS/ALES FORMULA SP4 BF LVT 30 RPM |
|---|---|---|---|---|---|---|---|---|
| 15 | APTAC-AcM | Polymer of Example 2 | 2 | 3300 | 93.3 | 98.45 | 94.67 | 4760/CLEAR/ MANY GELS PRESENT |
| 16 | MAPTAC-AcM | Polymer of Example 4 | 0.5 | 1720 | 43.54 | | | |
| 17 | APTAC-AcM | Polymer of Example 5 | 2 | 1360 | 87.51 | 93.83 | 81.57 | 4240/HAZY/ SOME GELS |
| 18 | APTAC-Acm | Polymer of Invention Example 8 | 2 | 1400 | 95.37 | 97.66 | 97.02 | 4300/CLEAR/ FEW GELS |
| 19 | APTAC-Acm | Polymer of Invention Example 9 | 2 | 800 | 95.91 | 98.13 | 95.63 | 3880/CLEAR/ SOME GELS |

[6]APTAC-AcM = acrylamidopropyltrmethyl ammonium chloride/acrylamide copolymer, MAPTAC = methacrylamidopropyl trimethylammonium chloride
[7]12% SLES(2EO)/2% CAPB; 1% Sodium Chloride; 0.2 wt % polymer
[8]Alkylpolyglucoside surfactant formulation; 0.2 wt % polymer
[9]Ammonium Lauryl Sulfate/Ammonium Laureth Sulfate surfactant formulation; 0.3 wt % polymer

Examples 15-19

The examples in Table 2 further demonstrate the improved shampoo clarity of the polymers of the invention. Polymers of the invention in Examples 18 and 19 show the best clarity, as demonstrated by % transmittance values>95% in three surfactant systems, with few to no gels. The comparative control polymer in Example 15 shows significant gels. The comparative control polymers in Examples 16 and 17 show significant gels, and reduced clarity as demonstrated by % transmittance values less than 90% in two of the three surfactant systems.

Examples 20-26

The enhanced deposition of antimicrobial actives and antifungal active compounds such as triclosan, zinc pyrithione and other zinc compounds, onto skin, hair and fabric substrates is of interest. In addition improved deposition efficiency of silicone and other conditioning oils and fragrances onto these substrates is also of interest. As shown in Table 3A, a model antidandruff shampoo containing a silicone emulsion (table 3B) and the polymer of the invention in Example 22 deposits more zinc onto an artificial skin substrate than the commercial antidandruff shampoo product in Example 20. In addition, the shampoo containing the polymer of the invention in Example 22 improved conditioning feel of the dry hair and reduced the "stringy" feel of the shampoo compared to the shampoo containing the higher MW cationic acrylamide in Example 21. In addition, the polymer of the invention in Example 23 delivers the higher combined zinc and silicone to the vitro-skin substrate. Comparison of Example 25 with 26 demonstrates that the lower MW polymer of Example 13 used in Example 25 delivers the higher combined zinc and silicone to the vitro-skin substrate for this terpolymer of the invention.

Examples 27-33

The examples in Table 4 demonstrate the improved silicone deposition onto hair for the shampoos containing blends of cationic guar with the cationic acrylamide, relative to the cationic guar polymer alone. The improvement was especially noted when the silicone concentration in the shampoo was reduced. As shown in Table 4, the blend composition of Example 30 and 31 deliver significantly more silicone to the hair at the 1.5 wt % silicone concentration than the individual cationic guar polymer, in Examples 29 while maintaining equivalent wet and dry comb performance to the cationic guar in example 29.

The distribution of the silicone on the hair tress is also of interest, in that generally, the silicone deposits more predominantly at the root end of the hair fiber, and less at the middle and tip sections of the tress where more conditioning is needed. As shown in Example 32 in Table 5, the shampoo of, Example 30 delivers a more desirable distribution of the silicone along the hair fiber, with less deposition at the root end of the fiber and more silicone deposition at the damaged hair fiber tip than the shampoo in Example 33 containing the cationic guar shampoo composition of Example 29.

The distribution of silicone along the length off the tress was measured according to the "silicone Mapping" procedure described in the methods section.

TABLE 3A

Conditioning Improvements in Model Shampoo Formula[10]

| Example | Polymer or Formulation | Zinc/Ppm deposited on Vitro Skin (Model Shampoo Table 3B.) | Dry Hair Sensory Comments (Model Shampoo Table 3B.) | Wet hair Shampoo Comments (Model Shampoo Table 3B.) | Zinc/Ppm deposited on Vitro Skin (Model Shampoo Table 3C.) | Silicone/Ppm deposited on Vitro Skin (Model Shampoo Table 3C.) |
|---|---|---|---|---|---|---|
| 20 | Head& Shoulders ® Shampoo[11] | 115 | Not conditioned | No comments | | 642 |
| 21 | Polymer Of Example 2-Comparative Example | 904 | Very conditioned | Very STringy | | |
| 22 | Polymer of the invention of Example 9 | 1022 | a little more conditioned, softer than Example 18 | Some Stringiness | | |
| 23 | Polymer of the invention of Example 9 | | | | 447 | 1051 |
| 24 | Comparative Hi MW Cat Acrylamide Polymer (Example 2) | | | | 642 | 748 |
| 25 | polymer of the Invention Example 13 | | | | 585 | 904 |
| 26 | Mid MW Polymer of Invention Example 14 | | | | 225 | 908 |

[10]Examples 21 through 26 prepared from formulation as described in US2007/0128147; DC 21491 silicone from Dow Corning Table 3B.; DC1784 from Dow Corning; Polymer present at 0.5 wt %
[11]Commercial Product from Procter & Gamble

TABLE 3B

Model Silicone Antidandruff Shampoo

| | | Active % | Shampoo % Basis | 100 g Shampoo | premix prep order of addition |
|---|---|---|---|---|---|
| Water | | 100% | 74.39 | 0.63 | 1 |
| SLES | Standapol ® ES2 | 25.5% | 10.00 | 39.22 | 2 |
| SLS | Rhodapon ® LCP | 29.7% | 6.00 | 20.20 | 3 |
| Cetyl alcohol | Crodacol ® C-95 NF | 100% | 0.60 | 0.60 | 5 |

TABLE 3B-continued

Model Silicone Antidandruff Shampoo

| | | Active % | Shampoo % Basis | 100 g Shampoo | premix prep order of addition |
|---|---|---|---|---|---|
| Cocamide MEA | Ninol ® CMP | 100% | 0.80 | 0.80 | 6 |
| Glycol distearate | Lexemul ® EGDS | 100% | 1.50 | 1.50 | 7 |
| Dimethicone pre-emulsion | DC 2-1491 | 40% | 1.49 | 3.73 | 11 |
| ZPT | Zinc Omadine ® FPS | 48% | 1.00 | 2.08 | 10 |
| Zinc Carbonate | Brueggeman Chemicals | 100% | 1.61 | 1.61 | 13 |
| Hydrochloric acid(6N) | | 100% | 0.18 | 0.18 | 4 |
| Magnesium Sulfate | | 100% | 0.28 | 0.28 | 9 |
| 25% sodium chloride | | 25% | 1.00 | 4.00 | 14 |
| Polymer | | 2% | 0.50 | 25.00 | 12 |
| Germaben II | Germaben II | 100% | 0.66 | 0.66 | 8 |

TABLE 3C

Model Silicone Microemulsion Antidandruff Shampoo

| | | Active % | Shampoo % Basis | 100 g Shampoo | premix prep order of addition |
|---|---|---|---|---|---|
| Water | | 100% | 74.39 | 0.63 | 1 |
| SLES | Standapol ® ES2 | 25.5% | 10.00 | 39.22 | 2 |
| SLS | Rhodapon ® LCP | 29.7% | 6.00 | 20.20 | 3 |
| Cetyl alcohol | Crodacol ® C-95 NF | 100% | 0.60 | 0.60 | 5 |
| Cocamide MEA | Ninol ® CMP | 100% | 0.80 | 0.80 | 6 |
| Glycol distearate | Lexemul ® EGDS | 100% | 1.50 | 1.50 | 7 |
| Dimethicone pre-emulsion | DC 1784 | 40% | 1.49 | 3.73 | 11 |
| ZPT | Zinc Omadine ® FPS | 48% | 1.00 | 2.08 | 10 |
| Zinc Carbonate | Brueggeman Chemicals | 100% | 1.61 | 1.61 | 13 |
| Hydrochloric acid(6N) | | 100% | 0.18 | 0.18 | 4 |
| Magnesium Sulfate | | 100% | 0.28 | 0.28 | 9 |
| 25% sodium chloride | | 25% | 1.00 | 4.00 | 14 |
| Polymer | | 2% | 0.50 | 25.00 | 12 |
| Germaben II | Germaben II | 100% | 0.66 | 0.66 | 8 |

TABLE 4

Effect of Polymer Blend on Comb Performance and Efficiency of Silicone Deposition[12]

| Example | Polymer Type | 1.5% Silicone in shampoo Silicone/ppm deposition hair | 0.75% Silicone in shampoo Silicone/ppm deposited on hair | 1.5% Silicone in shampoo Wet Comb Energy/gf-mm | 1.5% Silicone in shampoo Dry Comb Energy/gf-mm | 0.75% Silicone in shampoo Wet Comb Energy/gf-mm | 0.75% Silicone in shampoo Dry Comb Energy/gf-mm |
|---|---|---|---|---|---|---|---|
| 27 | No polymer control | | | | | | |
| 28 | Cationic guar Ashland Inc.[13] | 534 | | 4441 | 6659 | 3447 | 3327 |
| 29 | Cationic Guar Ashland Inc.[14] | 775 | | 3635 | 3202 | 3125 | 3929 |
| 30 | Blend of/cationic guar Polymer of Example 8 w Polymer of Example 23; Mw = 1.05E6 | 1390 | 423 | 3447 | 3327 | 3125 | 3929 |
| 31 | Blend of/cationic guar Polymer of Example 8 w Polymer of Example 23; Mw = 1.05E6 | 3642 | 1370 | 2536 | 1840 | 2822 | 2548 |

[12] 12% sodium laureth 2EO Sulfate/2% cocamidopropyl betaine, 1% sodium chloride, DC-1784 dimethicanol; 0.2 wt % Polymer

[13] N-Hance ® 3196 cationic guar offered by Ashland Inc.

[14] N-Hance ® 3215 cationic guar offered by Ashland Inc.

TABLE 5

Distribution of Silicone along Hair Fiber

| EX. | Polymer | Silicone/ppm depositon V. Brown hair | root | middle | tip |
|---|---|---|---|---|---|
| 32 | Polymer of Invention Formulation of Example 30 | 1390 | 0.45 | 0.6 | 0.45 |
| 33 | Formulation of Example 29 | 775 | 0.2 | 0.11 | 0.07 |

TABLE 6

Effect of Polymer on Extracted Weight of Deposit from Surfactant System[15]

| Example | Formulation | Polymer | Jojoba Oil On virgin brown Hair tress Avg Soluble wt. (g) | Stdev | Meadowfoam Seed Oil on virgin brown tress Avg Soluble wt (g) | Stdev | Jojoba Oil On Vitro Skin ppm |
|---|---|---|---|---|---|---|---|
| 34 | control no polymer | | 0.0011 | 0.0001 | 0.0009 | | 0 |
| 35 | shampoo-no polymer | | 0.0011 | 0.00015 | 0.00075 | 0.00005 | 0 |
| 36 | PQ-10[16] | | 0.0016 | 5E−05 | 0.00375 | 0.00015 | 0 |
| 37 | PQ-67[17] | | 0.0049 | 0.00125 | 0.00325 | 0.00155 | 0 |
| 38 | Cationic guar[18] | | 0.0043 | 0.00125 | 0.004 | 0.001 | 0 |
| 39 | Cationic guar[19] | | 0.0044 | 0.0001 | 0.0056 | 0.0004 | 200 |
| 40 | Polymer from Example 30 | Polymer of Invention | 0.0081 | 0.0002 | 0.01115 | 0.00085 | 0 |
| 41 | Polymer from Example 30 (Shampoo contained 30% less oil than Example 40) | Polymer of Invention | 0.0037 | 0.0004 | | | 0 |
| 42 | PQ-7[20] | | 0.0011 | 0 | 0.00395 | 5E−05 | 0 |
| 43 | Acrylamidoppropyltrimonium chloride/acrylamide copolymer[21] | Polymer of Invention | 0.008 | 0.0003 | 0.00725 | 0.00195 | 168 |
| 44 | Example 43 (Shampoo contained 70% less oil than Example 43) | Polymer of Invention | 0.0031 | 0.0005 | 0.007 | 0.0006 | 0 |
| 45 | Acrylamidoppropyltrimonium chloride/acrylamide copolymer[22] (refined jojoba oil) | Polymer of Invention | 0.0048 | 0.0002 | | | 0 |

[15] 12% Sodium laureth sulfate(2EO)/2% cocamidopropyl betaine/0.2 wt % Carbomer ® 980/1.5 wt % oil phase or as defined in table
[16] Polymer ® JR30M offered by Dow Chemical Company
[17] Softcat SX1300H offered by Dow Chemical Company
[18] NHance ® 3196 cationic guar offered by Ashland Inc.
[19] NHance ® 3215 cationic guar offered by Ashland Inc.
[20] Merquat ® 550 offered by Nalco.
[21] N-Hance SP-100 polymer; Mw = 8.75E5 offered by Ashland Inc.; charge density 1.85 meq/g
[22] N-Hance SP-100 polymer; Mw = 8.75E5 offered by Ashland Inc.; charge density 1.85 meq/g;

Examples 34-45

The unique enhanced deposition efficiency of the cationic synthetic polyelectrolyte polymers of the invention are further demonstrated by the results in Table 6 for conditioning surfactant compositions containing either jojoba oil or meadowfoam seed oil. As shown in Example 40, the polymer of the invention (same polymer as in Example 30) delivers the most jojoba and meadowfoam seed oil to the hair of all conditioning polymers in Table 6. The synthetic polyelectrolyte polymer of the invention in Example 43 also delivers a high amount of jojoba oil and nearly the same high amount of meadowfoam seed oil to the hair as the polymer in Example 43.

As shown on comparison of the results in Table 6 for Example 44 with Example 43, the synthetic polyelectrolyte polymer of the invention still delivers the same high amount of meadowfoam seed oil to the hair tress, even after reducing the amount of meadowfoam oil in the shampoo by 30%.

As shown in Table 6, Example 44, the surfactant system containing the synthetic polyelectrolyte polymer of the Invention also delivers a significant amount of jojoba oil to a synthetic skin model, after a washing procedure. Only the cationic guar in Example 39 delivered a similar amount of jojoba oil to the skin model substrate from this surfactant system.

Examples 46-60

The enhanced deposition of silicone onto bleached/damaged hair by the synthetic polyelectrolytes of the invention is shown in Tables 7 and 8. The shampoo formulation used for the examples in Table 7 is the same formulation used for the Examples in Table 6, containing a hydroxy-terminated silicone microemulsion. The polymer of the invention in Example 49 deposits 500-700 ppm silicone onto the bleached hair substrate. The polymer blends of the invention in Examples 50 and 51 deposit 200-300 ppm silicone onto the bleached hair substrate. The cationic guar polymer in comparative Example 48 deposits a maximum of 100 ppm silicone onto bleached hair substrate. The cationic hydroxyethyl cellulose in comparative Example 47 deposits a maximum of 28 ppm silicone onto the bleached hair substrate. The control shampoo deposits less than 10 ppm silicone onto the bleached hair substrate. These results demonstrate the improved conditioning and deposition performance of the polymers of the invention.

TABLE 7

Enhanced Deposition of Silicone oil onto Bleached and Virgin Brown Hair Substrates from a 2-in-1 Shampoo[23]

| | 46 Control | 47 Comparative Example[24] | 48 Comparative Example[25] | 49 Polymer of the Invention[26] | 50 Polymer of the Invention[27] | 51 Polymer of the Invention[28] | 49 Polymer of the Invention[29] |
|---|---|---|---|---|---|---|---|
| Silicone/ Avg. ppm Medium Brown hair | 30 | 29 | 1382 | 1545 | 1688 | 1626 | |
| Polymer | None | Polyquaternium-10 | Cationic guar | Acrylamidopropyl-trimonium chloride/ acrylamide copolymer | Blend cationic hydroxypropyl guar/ Acrylamidopropyl-trimonium chloride/ acrylamide copolymer | Blend cationic hydroxypropyl guar/ Acrylamidopropyl-trimonium chloride/ acrylamide copolymer | Acrylamidopropyl-trimonium chloride/ acrylamide copolymer |
| Silicone/ Avg. ppm Bleached hair | <10 | 27 | 97 | 562 | 195 | 291 | |

[23] 12% Sodium laureth sulfate(2EO)/2% cocamidopropyl betaine/0.4 wt % Carbomer ® 980/1.5 wt % Dow Corning 1784 silicone microemulsion
[24] Polyquaternium-10; Polymer ® LR400 offered by Dow Chemical Company
[25] Cationic guar offered as Jaguar ® by Rhodia Inc., charge density 1.3 meq/g; aq. Viscosity = cps at 1% polymer
[26] APTAC/Acm copolymer; offered as N-Hance by Ashland Inc.; charge density 1.85 meq/g; Mw = 8.75E5
[27] Blend APTAC/Acm copolymer; of Example 52 with cationic hydroxypropyl guar; Mw = 1.27E6
[28] Blend APTAC/Acm copolymer of Example 52 with cationic hydroxypropyl guar; Mw = 8.07E5. Offered as N-Hance ® HPCG by Ashland Inc.
[29] APTAC/Acm copolymer offered by Ashland Inc.; charge density 2.1 meq/g; Mw = 1.14E6

The Examples in Table 8B were prepared using the ingredients in Table 8A. The improved conditioned state of the brown hair samples treated with the shampoos containing the polymers of the invention in Examples 56 and 57 and the improved deposition of silicone by these formulations on bleached hair compared with the comparative examples in Table 8B demonstrate the invention.

TABLE 8A

Model Pearlescent 2-in-1 Conditioning Shampoo Formulation

| | | Active % | Shampoo % Basis | order of addition |
|---|---|---|---|---|
| Water | | 100% | 76.78 | 1 |
| SLES | Standapol ® ES2 | 25.5% | 10.00 | 2 |
| SLS | Rhodapon ® LCP | 29.7% | 6.00 | 3 |
| Cocamido-propyl betaine | Amphosol ® CA | 30% | 2.0 | 4 |
| Cocamide MEA | Ninol ® CMP | 100% | 0.50 | 7 |
| Glycol distearate | Lexemul ® EGDS | 100% | 1.50 | 8 (add at 74 C.) |
| Dimethicone pre-emulsion | 40/60 blend Path Silicones TBF-300K/TBF-350 as 63% actives emulsion in SLS surfactant + NaCl (mixed with IKA high shear mixer) | 63% | 1.0 | 10 (add at 30 C.) |
| Sodium Citrate | | 100% | 0.2 | 5 |
| Citric Acid | | 25% | 0.1 | 6 |
| Sodium Hydroxide | | 10% | As needed | 6a |
| 25% sodium chloride | | 25% | 1.00 | 11 |
| Polymer | | 1.5% | 0.25 | 12 |
| Germaben II | Germaben II | 100% | 0.66 | 9 |

TABLE 8B

Conditioning Performance of Pearlescent Model 2-in-1 Shampoos: Deposition of Silicone onto Hair[30]

| | Examples | | | |
|---|---|---|---|---|
| | 53 Comparative Example 0.125% AETAC-Acm[31] Polyquaternium-33 | 54 Comparative Example cationic guar[32] | 55 Comparative Example 0.2% Comparative Example: Blend of aqueous polymer solutions[33] | 56 Polymer of Invention 0.2% Blend[34] Cationic Guar/ AETAC-Acm Polyquaternium-33 |
| Shampoo pH @24 hr | 5.73 | 5.76 | 5.73 | 5.81 |

TABLE 8B-continued

Conditioning Performance of Pearlescent Model 2-in-1 Shampoos: Deposition of Silicone onto Hair[30]

| | | | | |
|---|---|---|---|---|
| Shampoo Viscosity @ 24 hr; (Brookfield LVT sp. 4/30 rpm 2 min. in jar) | 5280 | 4200 | 5340 | 4680 |
| Shampoo Comments | dense/rich foam, elastic | hardly any foam | very liitle foam, dense, a little elastic | elastic, hardly any foam |
| Dried brown tress comments | not very conditioned | not very conditioned | not very conditioned | conditioned |
| Silicone deposit/ppm on caucasian Virgin Brown Hair | 182 | 128 | 238 | 217 |
| Silicone deposit/ppm on Bleached Hair | 24 | 9 | 44 | 65 |

| | Examples | | | |
|---|---|---|---|---|
| | 57 Polymer of Invention 0.2% Blend Cationic Guar/ AETAC-Acm Polyquaternium-34 | 58 Comparative Example cationic guar of Example 48 | 59 Comparative Example cationic guar[35] | 60 Comparative Example cationic guar of Example 38 |
| Shampoo pH @24 hr | 5.84 | 5.79 | 5.84 | 5.77 |
| Shampoo Viscosity @ 24 hr; (Brookfield LVT sp. 4/30 rpm 2 min. in jar) | 5080 | 7700 | 5940 | 5840 |
| Shampoo Comments | dense/rich foam, elastic | very little foam, dense | less foam, dense | hardly any foam |
| Dried brown tress comments | conditioned | conditioned | conditioned | conditioned |
| Silicone deposit/ppm on caucasian Virgin Brown Hair | 194 | 89 | 218 | 120 |
| Silicone deposit/ppm on Bleached Hair | 56 | 30 | 27 | 40 |

[30] All polymer concentrations @ 0.25 wt %, except as shown
[31] AETAC/Acm: acryloxyethyltrimonium chloride/acrylamide copolymer offered as Flopam ® FO 4190SH by SNF
[32] N-Hance ® cationic guar offered by Ashland Inc., 0.8 meq/g; 1% aq viscosity = 45 cps
[33] Aqueous solution blend: 67 parts (Polymer of Example 51)/33 parts (acryloxyethyltrimonium chloride/acrylamide copolymer offered as Flopam ® FO4190SH by SNF
[34] Solid blend: 57 parts acryloxyethyltrimonium chloride/acrylamide copolymer offered as Flopam ® FO4190SSH by SNF/43 parts N-Hance 3270 cationic guar offered by Ashland
[35] Cationic guar offered as N-Hance BF17 by Ashland Inc.

Examples 61-63

Figure 2:
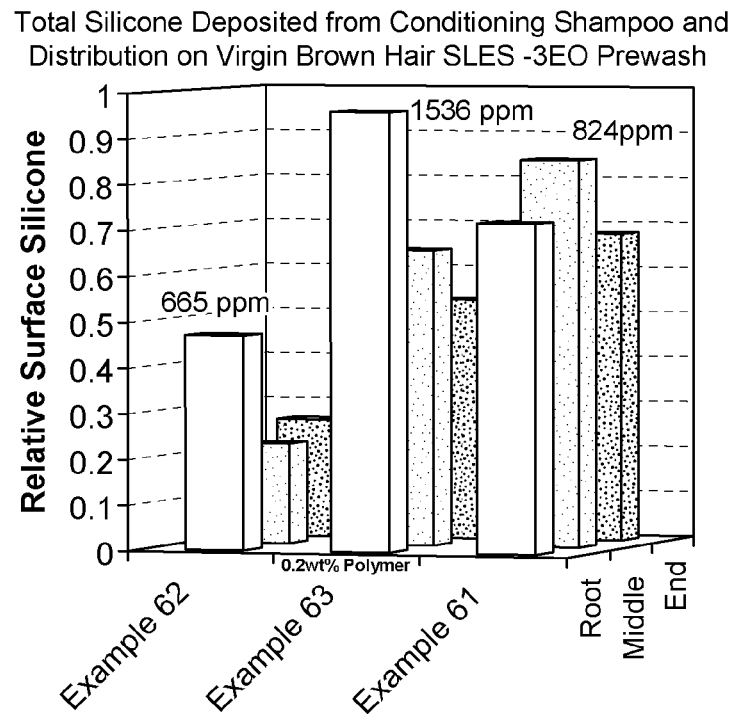
FIG. 2 is a graph showing total silicone deposited from conditioning shampoo and distribution on virgin brown hair SLES-3EO prewash.
Figure 3:
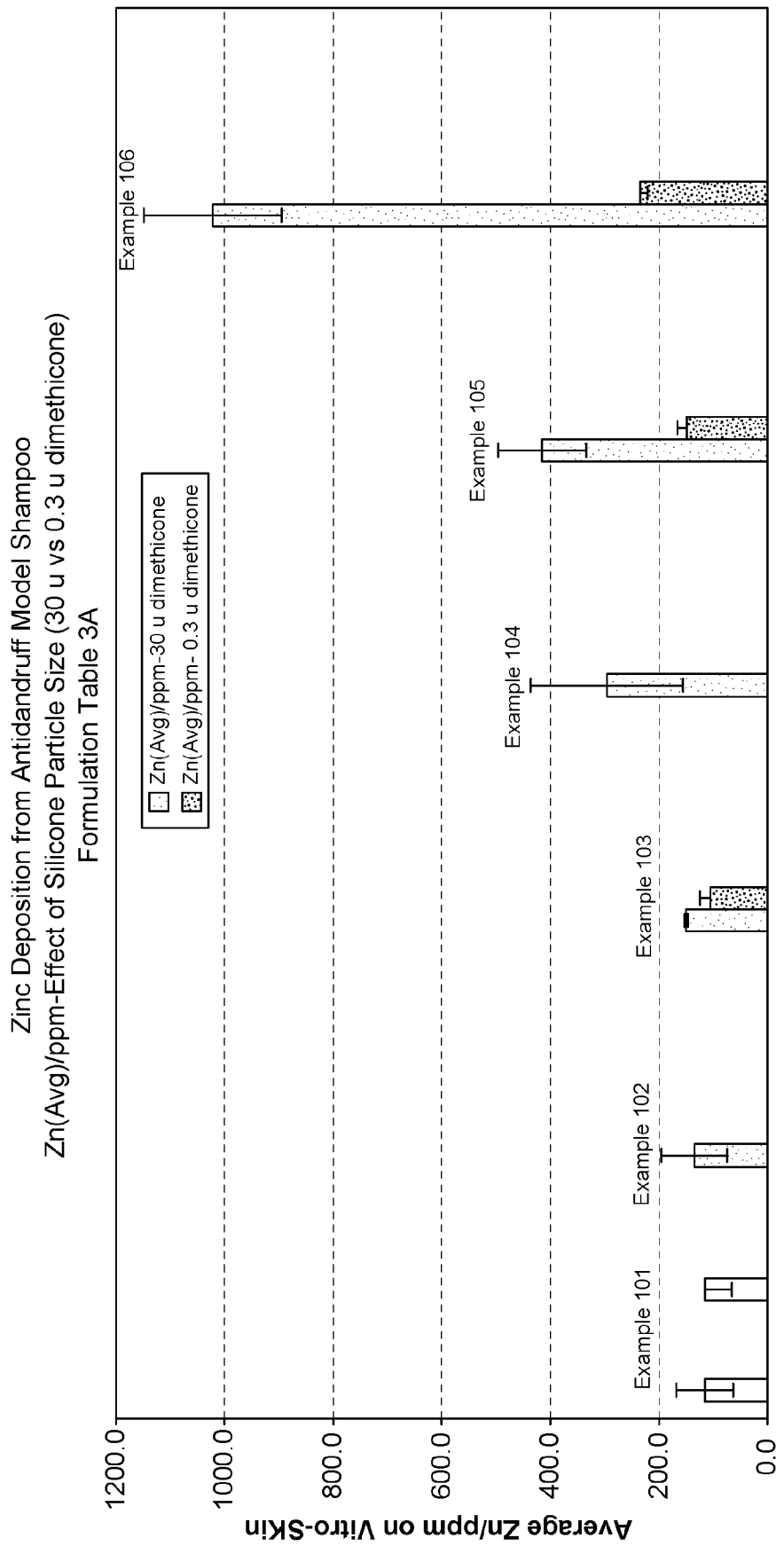
FIG. 3 is a graph depicting zinc deposition from antidandruff model shampoo Zn (Avg) ppm—effect of silicone particle size (30μ vs. 0.3μ dimethicone).

The unique deposition profile of silicone onto virgin brown hair from a 2-in-1 shampoo by the polymers of the invention are shown in FIGS. 1 and 2. In FIG. 1, the hair was prewashed with sodium laureth sulfate (2 EO) surfactant prior to treatment with the silicone 2-in-1 conditioning shampoo. In FIG. 2, the hair was prewashed with sodium laureth sulfate (3 EO) surfactant prior to treatment with the silicone 2-in-1 conditioning shampoo. Example 61 contains the polymer of the invention of Example 9. Example 62 contains the cationic guar polymer used in Example 10, and Example 63 contains the polymer of the invention in Example 12. The results in FIG. 1 demonstrate that the polymer of the invention in Example 12 deposits double the amount of silicone compared with the polymers of Example 9 and 10, onto the virgin brown tress, with more of the silicone spread along the hair fiber, to the middle and end of the tress. However in Example 61, the silicone is deposited more uniformly along the length of the tress, extending to the damaged tips of the hair tress.

TABLE 9

Effect of Polymer/Shampoo Treatment on Advancing and Receding Contact Angles for Virgin Brown Hair

| | Relative Silicone at | Fiber Diameter/ micron | | Contact Angle Adv./degrees | | Contact Angle Rec../degrees | |
|---|---|---|---|---|---|---|---|
| Example | Fiber end | Fiber 1 | Fiber 2 | Fiber 1 | Fiber 2 | Fiber 1 | Fiber 2 |
| 62 | 0.3 | 256 | 166 | 86.92 | 86.97 | 71.88 | 70.46 |
| 61 | 0.55 | 291 | 316 | 87.25 | 90.62 | 75.15 | 74.27 |

Single Fiber Contact Angle Measurements

As shown in Table 9, a higher contact angle is observed for the tip of the hair fibers treated with the shampoo of Example 61 compared with the hair treated with the shampoo of Example 62. This result is consistent with the tip of the hair fiber in Example 61 being more hydrophobic than the tip of the hair fiber for Example 62. This data supports the results in FIGS. 1 and 2, which indicate more silicone is delivered to the tip of the hair fiber by the shampoo in Example 61, which contains the polymer of the invention.

Examples 70-80

The polymers of the invention deliver amodimethicone conditioning agent to bleached hair from a 2-in-1 conditioning shampoo, as shown in Table 11. The lower wet comb energy values on bleached hair for hair treated with the shampoos containing the polymers of the invention in Examples 76, 77, 79, and 80 with the no polymer controls containing a cationic silicone in Example 70 and the amodimethicone in Example 71 demonstrates the conditioning delivered to the hair tress with the combination of amodimethicone and the

TABLE 10

Comb Performance of Conditioning Rinse Containing Polymers of Invention

| Components | Percent by weight | 64 | 65 | 66 | 67 | 68 | 69 |
|---|---|---|---|---|---|---|---|
| Deionized water | q.s. to 100 | Control | Polymer of Invention | Polymer of Invention | Polymer of Invention | Comparative Example | Comparative Example |
| Polymer (variable) | 1 | No Polymer | Polymer of Example 11 | Polymer of Example 30 | Polymer of Example 9 | Polymer of Example 29 | ElVive ® [36]Intense Smooth Conditioner |
| Natrosol plus 330S (2% sol.)- | | | | | | | |
| Ceteareth-20 | 0.5 | | | | | | |
| Ceateryl Alcohol | 4 | | | | | | |
| Amodimethicone | 1 | | | | | | |
| Euxyl PE9010 | 0.5 | | | | | | |
| Sodium Lactate/Lactic Acid | q.s. | | | | | | |
| BLEACHED HAIR | wet comb Energy gf-mm | 21787 | 1791 | 1570 | 1808 | 2953 | 1759 |
| BLEACHED HAIR | Dry comb Energy gf-mm | 1025 | 814 | 836 | 863 | 1245 | 1394 |

[36]Product offered by L'Oreal

Examples 64-69

As shown in Table 10, the polymers of the invention in Examples 65, 66, and 67, significantly reduce wet and dry comb energy for bleached hair treated with a conditioning rinse containing these polymers, compared to the control rinse (no polymer), compared to the cationic guar rinse in Example 68, and compared to the commercial conditioning rinse in Example 69.

polymers of the invention. The polymers of the invention in Examples 76, 77, 79, and 80 deliver more conditioning to bleached hair with the amodimethicone conditioning agent than the cationic cellulosic polymers in Examples 72 and 73.

The cationic guar polymers in Examples 74 and 75 also deliver good conditioning to bleached hair as evidenced by the low wet comb energies observed for these polymers.

Reducing the amodimethicone level by 50% (comparing Example 79 with 80 and Example 77 with 78), shows that the comb energy decreases for the polymer of Example 80 relative to Example 79, even after reducing the amodimethicone level by 50%. This result suggests that even further reduction of the amodimethicone can be achieved with the polymer of Example 80, while maintaining good conditioning performance.

Examples 81-101

Additional Polymers of the Invention were prepared as shown in Table 12. For a select set of these compositions, the zinc deposition onto a vitro skin substrate was examined using a modified version of formulation shown in Table 3A.

As shown in Table 12, the polymers of the invention in Examples 104-106 deposit more than twice the amount of zinc onto the vitro skin substrate compared to the commercial control antidandruff shampoo, and compared to commercial cationic guar polymers used for deposition. Decreasing the particle size of the silicone in the formulation does impact the amount of zinc deposited onto the vitro skin, however the polymers of the invention still outperform the commercial shampoo and the cationic guar benchmark polymers.

TABLE 11

Conditioning performance of Polymers of Invention with Amodimethicone 2-in-1 Conditioning Shampoo: Comb Energy Reduction on Bleached Hair

| Example | Polymer | wt % Amodimethicone DC 2-8194 | Wet comb BLEACHED | std deviation Wet Comb Bleached |
|---|---|---|---|---|
| 70 | None-Silicone Quat Ammonium DC 5-7113 Control | 1.5 | 10163 | 987 |
| 71 | None-Amodimethicone DC 2-8194 | 1.5 | 11750 | 2225 |
| 72 | PQ-10-Polymer of Example 36 | 1.5 | 5235 | 497 |
| 73 | PQ-67 Polymer of Example 37 | 1.5 | 6732 | 1427 |
| 74 | cationic guar Polymer of Example 38 | 1.5 | 2320 | 179 |
| 75 | cationic guar Polymer of Example 39 | 1.5 | 2604 | 337 |
| 76 | Polymer of the Invention Example 30 | 1.5 | 2776 | 357 |
| 77 | Polymer of the Invention Example 30 | 0.75 | 3609 | 245 |
| 78 | PQ-7 of Example 42 | 1.5 | 4169 | 975 |
| 79 | Polymer of the Invention, Example 43 | 1.5 | 3400 | 691 |
| 80 | Polymer of the Invention | 0.75 | 3166 | 410 |

TABLE 12

Blend Compositions of the Invention

| Example | Polymer | Parts per 100 parts of Polymer Example 49 | cationic guar Polymer of Example 54 = X | wt. polymer (g) | wt. water (g) | pH after stirring 2 hours | 24 hours pH after acid add | Brookfield LVT Viscosity/ cps sp. 3, 30 rpm 25 C | grams 25% citric/100 grams blend | Average CD, pH5 meq/g [37]solid | Average residual acrylam[38]de monomer[1]/ ppm | Average residual APTAC[39] monomer[2]/ ppm |
|---|---|---|---|---|---|---|---|---|---|---|---|---|
| 81 | Polymer of Invention | 20 | cationic guar Mw = 3.35e$^5$ charge density 0.8 meq/g | 1.0 | 99.0 | 9.7 | 5.4 | 72 | 9.7 | 1.15 | 10.5 | 42 |
| 82 | Polymer of Invention | 15 | cationic guar Mw = 3.35e$^5$ charge density 0.8 meq/g | 1.0 | 99.0 | 10.60 | 5.4 | 55.00 | 10.6 | 1.13 | 4 | 43 |
| 83 | Polymer of Invention | 10 | cationic guar Mw = 3.35e$^5$ charge density 0.8 meq/g | 1.0 | 99.0 | 11.40 | 5.40 | 49.00 | 11.4 | 1.03 | 3.5 | 13 |
| 84 | Polymer of Invention | 5 | cationic guar Mw = 3.35e$^5$ charge density 0.8 meq/g | 1.0 | 99.0 | 11.90 | 5.00 | 37.00 | 11.9 | 0.97 | 2.5 | 43 |
| 85 | Polymer of Invention | 30 | cationic guar Mw = 3.35e$^5$ | 1.0 | 99.0 | | 5.4 | 89.00 | | 1.27 | 15.5 | 59 |

TABLE 12-continued

Blend Compositions of the Invention

| | | | | | | | | | |
|---|---|---|---|---|---|---|---|---|---|
| 86 | Polymer of Invention | 30 | X charge density 0.8 meq/g | 1.0 | 99.0 | | | 84.00 | |
| 87 | Polymer of Invention | 50 (Polymer of Example 9) | X | 1.0 | 99.0 | 8.26 | 5.52 | 232 | 0.00 |
| 88 | Polymer of Invention | 30 | X | 1.0 | 99.0 | 8.72 | 5.51 | 120.0 | 0.03 |
| 89 | Polymer of Invention | 25 | X | 1.0 | 99.0 | 8.87 | 5.52 | 92.0 | 0.00 |
| 90 | Polymer of Invention | 20 | X | 1.0 | 99.0 | 8.95 | 5.54 | 72.0 | 0.04 |
| 91 | Polymer of Invention | 15 | X | 1.0 | 99.0 | 9.02 | 5.58 | 52.0 | 0.10 |
| 92 | Polymer of Invention | 10 | X | 1.0 | 99.0 | 9.11 | 5.47 | 40.0 | 0.00 |
| 93 | Polymer of Invention | 5 | X | 1.0 | 99.0 | 9.13 | 5.58 | 40.0 | 0.03 |
| 94 | Polymer of Invention | 50 | X | 1.0 | 99.0 | 8.26 | 5.52 | 232 | |
| 95 | Polymer of Invention | 70 | X | 1.0 | 99.0 | 7.16 | 5.50 | 412 | |
| 96 | Polymer of Invention | 75 | X | 1.0 | 99.0 | 6.72 | 5.49 | 472 | |
| 97 | Polymer of Invention | 80 | X | 1.0 | 99.0 | 6.30 | 5.32 | 512 | |
| 98 | Polymer of Invention | 85 | X | 1.0 | 99.0 | 5.52 | no | 560 | |
| 99 | Polymer of Invention | 90 | X | 1.0 | 99.0 | 4.81 | no | 604 | |
| 100 | Polymer of Invention | 95 | X | 1.0 | 99.0 | 4.22 | no | 624 | |

| Example | Polymer | Zn(Avg)/ppm-30u dimethicone | Standard Deviation | Median | Zn(Avg)/ppm-0.3u dimethicone |
|---|---|---|---|---|---|
| 101 | Commercial Head&Shoulders | 115.4 | 52.51 | 86 | |
| 102 | Polymer of Example 9 | 135 | | 120 | |
| 103 | Cationic Guar[40] | 150 | | | 105 |
| 104 | Polymer of Invention Example 88 | 250 | | | |
| 105 | Polymer of Invention[41] | 415 | | | 148 |
| 106 | Polymer of Invention Example 8 | 1022 | | | 235 |

[37] Measured by Mutek titration method with polyvinyl sulfonic acid
[38] Measured using liquid chromatography method, extraction of solid material with methanol.
[39] Measured using a liquid chromatography method
[40] Cationic guar offered as N-Hance BF17 by Ashland Inc.
[41] Polymer of Example 30 with 50 parts/100 of Polymer of Example 8.

Standard Testing Procedures

Wet and dry hair combinability measurements are typical test methods used to measure conditioning performance in shampoo and conditioner applications. In skin care applications, skin lubricity or reduced friction or softer feel of the skin, reduced water vapor transmission and improved skin elasticity are test methods used to measure skin conditioning. In surfactant-based household cleansing product formulations where conditioning performance is desired, such as dish detergents, fabric softeners, and antistatic products, conditioning refers to imparting a softer feel to fabric and eliminating static effects, eliminating fabric fiber breakage or deformation known as pilling. Imparting color retention properties to fabrics is also important and can be measured.

Silicone deposition onto hair tresses from shampoos and zinc deposition onto artificial skin can be measured by several techniques. One technique used for quantifying silicone deposition onto hair and one technique quantifying zinc deposition onto solid substrates such as artificial skin are described below.

Silicone Deposition Measurement

Each 2-5 gram hair tress sample was weighed to the nearest mg, after removal of sample holder, and placed into clean 8 oz jars with approximately 150 ml of methylene chloride. The samples were shaken for 1.5 hours at room temperature. The methylene chloride supernatant was filtered using Whatman #41 filter paper and quantitatively transferred to clean 8 oz jars and evaporated to dryness with mild heat and a nitrogen sparge. Each sample was then dissolved into 2 ml of chloroform-d and quantitatively transferred to a 5-ml volumetric flask. Three chloroform-d rinses were used to transfer each sample to the 5-ml volumetric flask. All flasks were diluted to the mark with solvent and inverted. Each sample was examined in a NICOLET MAGNA 550 FT-IR with 150 co-added scans at 4 cm-1 resolution and 0.4747 velocity using a 0.1 cm-fixed path salt cell. A chloroform-d reference spectrum was used to subtract out the solvent bands (diff=1.0). The silicone level was determined by measuring the peak height of the Si—CH3 stretch at 1260 cm-1 (baseline 1286 and 1227 cm-1) followed by conversion to mg/ml of silicone using a low level calibration curve extending from 10-300 parts per million (ppm). Each sample was corrected for dilution volume and sample weight. All values are reported to the nearest ppm.

Silicone Mapping Along Tress Length

The relative concentration of the silicone deposit was mapped using a surface infrared technique, attenuated total reflectance-infrared spectroscopy (ATR-IR). This technique can be used to qualitatively map the surface deposition of silicone along the hair fiber The ATR accessory is most commonly used with a Fourier transform infrared (FTIR) spectrometer and referred to as FTIR/ATR. The technique is a surface analysis method that may very in depth of the analyte studied from ~0.3 µm to 4 or 5 µm depending on several factors including ATR crystal angle, refractive index of the ATR crystal, and refractive index of the sample. This technique measures the relative amount of silicone in the surface layer to a depth of 3 µm. The ATR-IR technique used in this study uses the ratio of the peak height of the silicone band near 796.5 cm$^{-1}$ (tangent baseline), to an area slice of a hair reference band from 940.1 cm$^{-1}$ to 919.9 cm$^{-1}$ (tangent baseline) to determine the relative surface silicone level according to equation 1. This method of surface silicone measurement was shown to have a correlation with total extracted silicone levels across a range of 300 ppm to 4000 ppm.

Ratio: Peak Height at 796.5 cm$^{-1}$/Peak Area (940.1 cm$^{-1}$ to 919.9 cm$^{-}$=Relative Surface Silicone Level (detection limit=0.05)     (eq 1)

The technique may be used to measure approximately 10-20 strands of hair in one measurement with a 1 mm circular spot. A bundle of fibers from each tress is positioned on a Golden Gate* diamond ATR accessory of the Thermo-Nicolet MAGNA* 760 FTIR spectrometer equipped with a deuterated triglycine sulfate, (DTGS) detector. Infrared spectra are collected at 12 different locations on the hair tress starting from the top and working towards the bottom of the tress.

Zinc and Conditioning Oil Deposition Measurement of Zinc on Vitro-Skin Samples One gram of shampoo is layered on top of twenty grams of water in a 30 ml glass jar. The mixture is stirred for 10 seconds using a magnetic stir bar. The mixture is poured onto the center a 2.5 cm square of Vitro-Skin® (IMS Inc., Portland, Me.) that has been prehydrated (per manufacturer instructions), then prewetted with deionized water on a Buchner funnel. The liquid is filtered through the Vitro-Skin under gravity filtration. The Vitro-Skin is rinsed with three rinses of deionized water (50 ml @ 40 C) under gravity filtration, with the third rinse under aspirator vacuum. The Vitro-skin sample is then removed from the funnel to air dry overnight at ambient temperature. The Vitro-Skin sample is then analyzed for zinc using X-ray fluorescence.

Jojoba and Meadowfoam Seed Oil Deposit-Quantification

The hair tresses or Vitro Skin samples were weighed and extracted 2× with 100 ml of heptane. The two extract solutions were combined and evaporated to dryness and the weight recorded.

Single Fiber Tensiometer Measurements

The hydrophobicity of the tip end of hair treated with 2-in-1 conditioning shampoo was determined using a Kruss[42] K100SF single fiber tensiometer to measure the wettability of the hair tip as it is immersed in water.

[42] Trademark owned by a third party.

Wet/Dry Comb Performance Measurement—Virgin Medium Brown European Hair and Lightly Bleached European Medium Brown Hair Conditions Measured at constant temperature and humidity (72° F. and 50% relative Humidity).
Equipment:
Instron 1122 (2-lb. load cell, 500-gram range used)
Prewash Procedure:

Each tress was washed twice with sodium lauryl sulfate, SLS, or other anionic surfactants, e.g., sodium lauryl ether sulfate (SLES) using 0.1 g-5 g surfactant/gram tress, washing twice then air drying overnight at 73° F. and 50% relative humidity. The twice washed tress was hand combed 5-times with large teeth comb and 5-times with small teeth comb. (10× total).

The following combing protocol was used for bleached and virgin hair. Two to three tresses were used, and the average reported from the two to three tresses combed 8 times per tress, with more precombing of the tresses prior to measurement as described above.

Shampoo Procedure

1. Each tress was shampooed twice with 0.1 g shampoo per 1 gram tress (all tresses were 3.0 g)
2. Each shampooed tress was hand combed twice with a large teeth comb.
3. The hand combed tress was loaded into a Instron instrument and the crosshead was lowered to bottom stop. The tress was combed twice with small teeth comb and placed into double-combs.

The Instron was run under standard conditions.

After the test was run, the tress was sprayed with DI water to keep moist.

4. After the eight tests were finished, the tress was hung up overnight.
5. The next day, each tress was dry combed tested eight times. No hand combing of dry tresses was done.
6. Averaged wet comb energy for 16 Instron runs and reported average with standard deviation.
7. Averaged dry comb energy for 16 Instron runs and reported average with standard deviation.

HPLC Ion-Exclusion Method for Measurement of Residual Acrylamide Monomer in Cationic Polyacrylamide Polymers This method was developed for the determination the residual unreacted acrylamide in cationic acrylamide polymers. The method employs a Bio-Rad Aminex HPX 87H column and an isocratic mobile phase (0.1N sulfuric acid in water).

Detection is accomplished using a UV detector at 200 nm.

Apparatus (1) Liquid chromatograph—Agilent 1200 Series Quaternary LC System with diode array detector, autosampler, thermostatted column compartment and ChemStation software or equivalent, available from Agilent Technologies, 2850 Centerville Road BU3-2, Wilmington, Del. 19808-1610, www.agilent.com/chem.
(2) Bio-Rad Aminex HPX-87H, 300 mm×7.8 mm, available from Bio-Rad Laboratories, Inc., 2000 Alfred Nobel Drive, Hercules, Calif. 94547, www.bio-rad.com, Cat. No. 125-0140.
(3) Branson 220 sonic bath, available from Branson Cleaning Equipment Company, Parrott Drive, Shelton, Conn. or equivalent.
(5) Autosampler vials, 2 mL, available from VWR International, Cat. No. 5182-0555 or equivalent.
(6) Vortex, model G-560 Genie 2—Ibid or equivalent.
(7) Analytical Balance, capable of weighing 0.1 g to the nearest 0.00001 g (100 milligrams to the nearest 0.01 milligram), Mettler-Toledo AX205 or equivalent.

Reagents (1) Deionized water, high purity—use the highest purity water available. The deionized water can be prepared via an ion exchange purifier such as the Milli-Q Reagent Water System, Millipore Corporation, 290 Concord Rd., Billerica, Mass. 01821. Bacterial growth must be avoided.
(2) Burdick & Jackson HPLC Grade Acetonitrile—available from Honeywell Burdick & Jackson, 101 Columbia Road, Morristown, N.J. 07962, Cat. No. 015-4.
(3) Acrylamide—99+%, electrophoresis grade—available from Sigma-Aldrich, www.sigma-aldrich.com, Cat. No. 148660-500G.
(4) Phosphoric Acid, 85%, ACS Reagent grade ($H_3PO_4$, CAS 7664-38-2)—Ibid, Cat. No. 466123-25G or equivalent.
(5) Extraction Solution—Mix 800 mL of Burdick & Jackson grade Acetonitrile with 200 mL of high purity deionized water. Allow solution to adjust to room temperature.

Instrument Operating Parameters

| Column | Bio-Rad Aminex HPX-87H, 300 mm × 7.8 mm |
| --- | --- |
| | Mobile PhaseIsocratic, 0.01 N Sulfuric Acid in Water |
| Flow | 0.5 mL/min. |
| Column Temp. | 50° C. |
| Injection Volume | 50 μL |
| Detector | |

Diode array, wavelength monitored: 200 nm, reference wavelength: 550 nm with band widths of 100 nm.

Calibration (1) Weigh ~0.02 g of Acrylamide to the nearest 0.0001 g into a 100-mL volumetric flask.
(2) Fill to the mark with extraction solution (reagent 5), 80/20 Acetonitrile/Water.
(3) Shake to dissolve the acrylamide. This will yield ~0.2 mg/mL solution of acrylamide
(4) Pipet 1 mL of the above solution into a 100 mL volumetric flask.
(5) Fill to the mark with extraction solution (reagent 5), 80/20 Acetonitrile/Water.
(6) Shake to mix solution. This will yield ~0.002 mg/mL solution of acrylamide.
(7) With the chromatograph at operating conditions, inject a blank (reagent 5).
(8) With the chromatograph at operating conditions, inject the acrylamide standard solution.
(9) Determine the peak area for the acrylamide in the chromatogram of the standard solution. A chromatogram of a standard solution is shown in FIG. 1.

Procedure (1) Weigh ~0.1 g of the sample to the nearest 0.0001 g into a 17 mL vial.
(2) Pipet 5 mL of 80/20 Acetonitrile/Water (reagent 5) into the vial.
(3) Place the sample in a sonic bath for 15 minutes.
(4) Vortex to mix and allow sample to equilibrate to room temperature.
(5) Decant the liquid (filter if necessary) into an HPLC autosampler vial.
(6) With the chromatograph at operating conditions, inject the sample solution.
(7) Identify the peak corresponding to acrylamide in the chromatogram and determine the peak area. A chromatogram of a sample is shown in FIG. 2.

Calculations $$\frac{As \times Crs}{Ars \times Cs} \times 100\% = \text{Wt \% Acrylamide}$$

where:
As=area of the Acrylamide peak found in the sample chromatogram
Crs=concentration of the Acrylamide (mg/mL) in the reference standard solution
Ars=area of the Acrylamide peak found in the reference standard chromatogram Cs=concentration (mg/mL) of the sample
Report
Report the Wt % of Acrylamide in the sample to the nearest 0.0001%.

Several examples of the above technologies were demonstrated in the following Examples 1-6 in shampoo Formulation I, Table 1, using the standard combing protocol on bleached hair and virgin brown hair. This formulation is shown only for example and other formulations containing other silicones, or other oils, such as mineral oil or any other commonly used conditioning oil, humectants such as glycerol, or conditioning ingredients, such as panthenoic acid or derivatives can be included.

Molecular Weight

Weight average molecular weights were determined using aqueous size exclusion chromatography.

Size Exclusion Analysis Conditions for Cationic polymers

The polymer was dissolved in the mobile phase at a concentration of about 2 mg/ml, and a volume of 0.15 ml was injected onto the column.
Mobile Phase: 0.2 M Sodium chloride/0.1% Trifluoroacetic acid at pH 2
Flow Rate: 0.8 ml/min
Columns: Suprema Max pre-column+3000 Å+100 Å (8.0 mm×300 mm, 10 µm) columns in series
Column Temperature: 35° C.
DRI Detector Temperature: 35° C.
Light scattering photometer: sensitivity×100
Sample concentration: Typically 2 mg/ml (0.2%, unless otherwise noted), in mobile phase
Sample preparation: Stir in mobile phase for a minimum of 1-2 hours
Sample solution appearance: clear; make note if turbid
Filtration: 0.45 µm PVDF membrane filter; make note if difficult to filter The cationic water-soluble synthetic polyelectrolyte compositions can deposit with high efficiency on substrates such as hair, skin, teeth, oral mucosa, or textile fabrics and can impart benefits to the substrates. Upon deposition onto the substrate, the cationic water-soluble synthetic polyelectrolyte compositions can also deposit other ingredients, which improve the condition or enhance the characteristics of the substrate. The cationic water-soluble synthetic polyelectrolyte compositions of use in the present invention also have potential for conditioning skin from cleansing formulations or moisturizing formulations, since these polymers may also better deliver the oil phase typically used in creams and lotions.

Surprisingly, it has been found that cationic water-soluble synthetic polyelectrolyte compositions are useful in performing as deposition agents without imparting unacceptable "stringy" characteristics to surfactant-based formulations. The cationic water-soluble synthetic polyelectrolyte compositions perform as deposition agents with reduced buildup on hair from surfactant systems, improved uniformity of silicone deposition along the hair fiber on all hair types, including damaged hair or bleached hair, improved lubricity or softness of hair, as measured by dry comb and friction measurements, when delivered from silicone and nonsilicone shampoos, and for improved deposition of other active materials, such as colors or dyeing agents, zinc pyrithione, fragrance, antimicrobial materials, etc., onto the scalp and the hair. The cationic water-soluble synthetic polyelectrolyte compositions can be combined with non-cellulosic cationically modified polysaccharides as part of their composition. This combined polymer composition can deposit with high efficacy and impart uniformity to deposits applied onto hair/skin and can impart great conditioning benefits to keratin substrates. Such polymers impart other benefits in hair styling, body lotions and sunscreens.

Although the invention has been described with referenced to preferred embodiments, it is to be understood that variations and modifications in form and detail thereof may be made without departing from the spirit and scope of the claimed invention. Such variations and modifications are to be considered within the purview and scope of the claims appended hereto.

What is claimed is:

1. A cationic polyelectrolyte formulation including:
1) a solid cationic synthetic water soluble polyelectrolyte comprising a polymer formed from (meth)acrylamide and one or more of i) a cationic (meth)acrylamide monomer, and ii) a cationic (meth)acrylic acid monomer, and iii) hydrolysis stable cationic monomers wherein said polyelectrolyte has a molecular weight less than 2 million and a charge density of 0.001 meg/g to 2.5 meq/g and a level of unreacted acrylamide monomer less than 50 ppm;
2) a surfactant;
3) a solvent, and;
4) wherein said cationic synthetic water soluble polyelectrolyte is formed by adiabatic gel polymerization and is subsequently milled to a particle size of 50 to 60 µm to provide said level of unreacted acrylamide of less than 50 ppm.

2. The composition claimed in claim 1 further including one active personal care ingredient or benefit agent.

3. The composition claimed in claim 2 further comprising a noncellulosic cationic polysaccharide.

4. The composition claimed in claim 3 wherein the polysaccharide is selected from the group consisting of guar, locust bean, tam, honey locust, cassia gum, flame tree, xanthum gum, gellan gum, wellan gum, rhamsan gum; konjac, mannan, gum acacia, soy polysaccharide, xylofructose gums, alginate and tamarind gum.

5. The composition claimed in claim 3 wherein said active personal care ingredient or benefit agent includes a conditioning agent.

6. The composition claimed in claim 5 wherein said agent is a silicone oil, jojoba oil, meadowfoam seed oil, seed oils, glycerin, emollient, or moisturizing agent.

7. The composition claimed in claim 3 wherein said active ingredient includes an antidandruff agent.

8. The composition claimed in claim 7 wherein said antidandruff agent is zinc pyrithione, selenium, or an antimicrobial compound.

9. The composition claimed in claim 1 comprising 0.01 to 30% by weight of said cationic synthetic water soluble polyelectrolyte.

10. The composition claimed in claim 1 comprising 0.01 to 50% surfactant.

11. The composition claimed in claim 10 wherein said surfactant is selected from a group consisting of anionic, cationic, nonionic, zwitterionic, amphoteric, gemini, and combinations thereof.

12. The composition claimed in claim 1 comprising 0.01 to 99% solvent.

13. The composition claimed in claim 1 wherein said polyelectrolyte has a level of unreacted monomer of 10.5 ppm or less.

14. A cationic polyelectrolyte formulation including:
1) a solid cationic synthetic water soluble polyelectrolyte comprising a polymer formed from (meth)acrylamide and one or more of i) a cationic (meth)acrylamide monomer, and ii) a cationic (meth)acrylic acid monomer, and iii) hydrolysis stable cationic monomers wherein said polyelectrolyte has a weight average molecular weight less than 2 million and a charge density of 0.001 meg/g to 2.5 meq/g and wherein said polyelectrolyte is formed by adiabatic gel polymerization and is subsequently milled to a particle size of 50 to 60 µm to provide a level of unreacted acrylamide monomer less than 50 ppm;
2) a surfactant;
3) a solvent, and
4) a noncellulosic cationic polysaccharide.

15. The composition claimed in claim 14 having a ratio of synthetic water soluble polyelectrolyte to polysaccharide of 5:95 to 95:5 by weight.

16. The composition claimed in claim 15 wherein said active ingredient includes a benefit agent.

17. The composition claimed in claim 14 wherein said benefit agent is silicone oil, jojoba oil, or meadowfoam seed oil.

18. A method of depositing an oil onto a surface comprising applying a composition comprising:
1) a solid cationic synthetic water soluble polyelectrolyte comprising a polymer formed from (meth)acrylamide and one or more of i) a cationic (meth)acrylamide monomer, and ii) a cationic (meth)acrylic acid monomer, and iii) hydrolysis stable cationic monomers wherein said polyelectrolyte has a weight average molecular weight less than 2 million and a charge density of 0.001 meg/g to 2.5 meq/g and wherein said cationic synthetic water soluble polyelectrolyte is formed by adiabatic gel polymerization and is subsequently milled to a particle size of 50 to 60 µm to provide a level of unreacted acrylamide of less than 50 ppm;
2) a surfactant;
3) a solvent,
4) an active personal care ingredient or benefit agent and
5) a cationic polysaccharide
onto a surface;
diluting said composition with water to form a diluted solution on said surface;
and
rinsing said diluted solution from said surface.

* * * * *

UNITED STATES PATENT AND TRADEMARK OFFICE
CERTIFICATE OF CORRECTION

PATENT NO. : 8,343,469 B2
APPLICATION NO. : 12/828853
DATED : January 1, 2013
INVENTOR(S) : Patric Bierganns et al.

It is certified that error appears in the above-identified patent and that said Letters Patent is hereby corrected as shown below:

In the Specifications:

Column 7, Line approximately 55, "with $C_1$ to in the alkyl"    should read    --with $C_1$ to $C_3$ in the alkyl--

Column 17, footnote 6, "acrylamidopropyltrmethyl ammonium"    should read    --acrylamidopropyltrimethyl ammonium--

Column 23, Table 6, Example #43, "Acrylamidoppropyltrimonium"    should read    --Acrylamidopropyltrimonium--

In the Claims:

Claim 4, Column 40, line 39, "locust bean, tam, honey locust"    should read    --locust bean, tara, honey locust--

Signed and Sealed this
Thirtieth Day of April, 2013

Teresa Stanek Rea
*Acting Director of the United States Patent and Trademark Office*